United States Patent

Eleckenstein et al.

[11] 3,956,294
[45] May 11, 1976

[54] SUBSTITUTED PYRIDINE COMPOUNDS

[75] Inventors: Erwin Eleckenstein, Hofheim, Taunus; Ernst Heinrich, Frankfurt am Main-Fechenheim; Reinhard Mohr, Offenbach-Rumpenheim, all of Germany

[73] Assignee: Cassella Farbwerke Mainkur Aktiengesellschaft, Germany

[22] Filed: Nov. 6, 1974

[21] Appl. No.: 521,443

Related U.S. Application Data

[62] Division of Ser. No. 372,024, June 21, 1973.

[30] Foreign Application Priority Data

June 22, 1972    Germany............................ 2230392

[52] U.S. Cl.................. 260/246 B; 260/247.1 M;
260/247.5 D; 260/247.5 EP; 260/247.5 G;
260/268 BC; 260/268 H; 260/268 C;
260/293.63; 260/293.64; 260/293.69;
260/294.8 F; 260/294.9; 260/156; 424/250;
260/294.8 G; 260/294.8 R
[51] Int. Cl.²....................................... C07D 295/12
[58] Field of Search........ 260/294.9, 246 B, 293.69,
260/293.63, 293.64, 247.1 M, 268 BC, 268
H, 242.50, 247.5 EP, 247.5 G, 294.8

[56] References Cited
UNITED STATES PATENTS 3,853,895   12/1974   Lamm et al..................... 260/294.9

*Primary Examiner*—Joseph A. Narcavage
*Assistant Examiner*—Jose Tovar
*Attorney, Agent, or Firm*—Connolly and Hutz

[57] ABSTRACT

Compounds of the formula

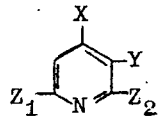

wherein X is aliphatic, cycloaliphatic, aromatic, aralkyl, hetaryl, hetarylalkyl or hydrogen; Y is aliphatic, aromatic, aralkyl, $-COOR_2$, $-COR_2$,

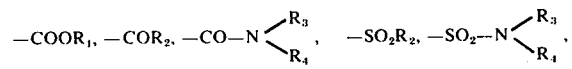

$-CN$, $-NH_2$, $-NO$, $-NO_2$ or hydrogen with the proviso that when Y is hydrogen, X is other than hydrogen; $Z_1$ is cyano,

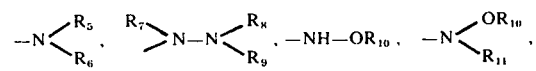

$-OR_{12}$, $-SR_{12}$ or $-SO_2R_{12}$ and $Z_2$ is chlorine, bromine, cyano, hydroxy, mercapto,

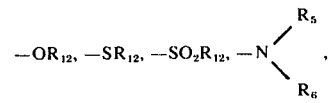

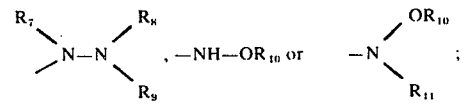

$R_1$ is aliphatic; $R_2$ is aliphatic, cycloaliphatic, aromatic, aralkyl or heterocyclic; $R_3$ and $R_4$ when taken separately are hydrogen, aliphatic, cycloaliphatic, aromatic or aralkyl; $R_3$ and $R_4$ when taken together with the nitrogen atom to which they are attached form a heterocyclic moiety; $R_5$ and $R_6$ when taken separately are aliphatic, aromatic, aralkyl, heterocyclic or hydrogen; $R_5$ and $R_6$ when taken together with the nitrogen atom to which they are attached are heterocyclic; $R_7$ is hydrogen; aliphatic or aromatic; $R_8$ and $R_9$ are aliphatic or aromatic, $R_{10}$ is hydrogen, aliphatic or aralkyl, $R_{11}$ is aliphatc and $R_{12}$ is aliphatic, aromatic or aralkyl; $R_{10}$ and $R_{11}$ when taken together with the nitrogen atom to which they are attached are heterocyclic.

10 Claims, No Drawings

SUBSTITUTED PYRIDINE COMPOUNDS

CROSS-REFERENCE TO RELATED APPLICATION

This application is a division of application Ser. No. 372,024 filed June 21, 1973.

This invention relates to compounds of the formula

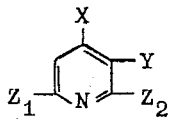 I wherein X is alkyl having 1 to 6 carbon atoms, alkenyl having 2 tp 6 carbon atoms, cycloalkyl having 3 to 8 carbon atoms, heteroaryl having 4 to 7 carbon atoms and containing one or two heteroatoms selected from the group of O, N and S, phenyl, benzyl, phenethyl, one of said radicals substituted as hereinafter defined or hydrogen; Y is alkyl having 1 to 6 carbon atoms, alkenyl having 2 to 6 carbon atoms, cycloalkyl having 3 to 8 carbon atoms, phenyl, benzyl, phenethyl, one of said radicals substituted as hereinafter defined, —COOR$_1$, —COR$_2$,

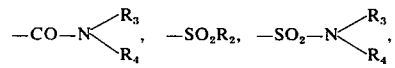

—CN, —NH$_2$, —NO, —NO$_2$ or hydrogen with the proviso that when Y is hydrogen, X is other than hydrogen; Z$_1$ is cyano,

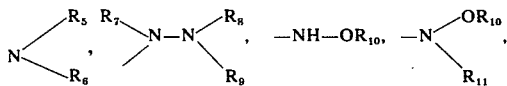

—OR$_{12}$, —SR$_{12}$ or —SO$_2$R$_{12}$ and Z$_2$ is chlorine, bromine, cyano, hydroxy, mercapto, —OR$_{12}$, —SR$_{12}$, —SO$_2$R$_{12}$,

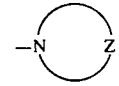

R$_1$ is alkyl having 1 to 6 carbon atoms, alkenyl having 2 to 6 carbon atoms or one of said radicals substituted as hereinafter defined; R$_2$ is alkyl having 1 to 6 carbon atoms, alkenyl having 2 to 6 carbon atoms, cycloalkyl having 3 to 8 carbon atoms, phenyl, benzyl, phenethyl, pyridyl, thiazolyl, benzothiazolyl, imidazolyl, benzimidazolyl, thienyl, furyl or pyrrolyl, one of said radicals substituted as hereinafter defined; R$_3$ and R$_4$, when taken separately, are alkyl having 1 to 6 carbon atoms, cycloalkyl having 3 to 8 carbon atoms, phenyl, benzyl, phenethyl, one of said radicals substituted as hereinafter defined or hydrogen; R$_3$ and R$_4$, when taken together with the nitrogen atom to which they are attached, form a piperidino, piperazino, morpholino, or ethyleneimino radical; R$_5$ and R$_6$, when taken separately, are alkyl having 1 to 6 carbon atoms, cycloalkyl having 3 to 8 carbon atoms, phenyl benzyl, phenethyl, pyridyl, thi-azolyl, benzothiazolyl, imidazolyl, bemzimidazolyl, pyrrolyl, one of said radicals substituted as hereinafter defined or hydrogen; R$_5$ and R$_6$ when taken together with the nitrogen atom to which they are attached, form a piperidino, piperazino, morpholino or ethyleneimino radical; R$_7$ is hydrogen, alkyl having 1 to 6 carbon atoms, phenyl or phenyl substituted as hereinafter defined; R$_8$ and R$_9$ are alkyl having 1 to 6 carbon atoms, phenyl or phenyl substituted as hereinafter defined; R$_{10}$ is alkyl having 1 to 6 carbon atoms, benzyl, phenethyl, one of said groups substituted as hereinafter defined or hydrogen; R$_{11}$ is alkyl having 1 to 6 carbon atoms or said alkyl substituted as hereinafter defined; R$_{12}$ is alkyl having 1 to 6 carbon atoms, alkenyl having 2 to 6 carbon atoms, cycloalkyl having 3 to 8 carbon atoms, phenyl, benzyl, phenethyl or one of said radicals substituted as hereinafter defined; the substituents for substituted alkyl or alkenyl radicals specified hereinabove being selected from the group consisting of cyano, hydroxy, acetoxy, phenoxyacetoxy, alkoxy having 1 to 2 carbon atoms, phenoxy, monoalkylamino having 1 to 4 carbon atoms, dialkylamino having 1 to 4 carbon atoms in each alkyl moiety, N-ethylcarbamoyloxy, N-methylcarbamoyloxy, N-phenylcarbamoyloxy, acetylamino, benzoylamino, heteroaryl having 4 to 7 carbon atoms and containing one or two heteroatoms selected from the group of O, N and S, and

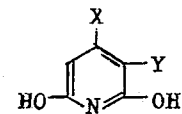

wherein Z constitutes the atoms completing a morpholino, piperidino, piperazino, N-methyl-piperazino or cyclopentamethyleneimino group and the substituents for the substituted cycloalkyl, phenyl, benzyl, phenethyl and heterocyclic radicals specified hereinabove being selected from the group consisting of bromine, chlorine, cyano, alkyl having 1 to 3 carbon atoms and alkoxy having 1 to 2 carbon atoms. The above-mentioned heteroaryl residues having 4 to 7 carbon atoms may be pyridyl, thiazolyl, benzthiazolyl, imidazolyl, benzimidazolyl, thienyl, furyl or pyrrolyl groups.

The starting materials for the preparation of the novel compounds of formula I are 2,6-dihydroxypyridine derivatives of the formula:

II wherein X and Y having the above-stated meaning. These starting compounds may be prepared in a known manner analogous to the method described by Bobbitt and Scola, Journ. of Org. Chem. 25, 560: by the condensation of correspondingly substituted acetic acid amides with correspondingly substituted β-ketocarboxylic acid esters. They may also be prepared in accordance with various other processes, as described for example in the monograph "Heterocyclic Compounds Pyridine and its Derivatives Part. 3" by Klingsberg. This monograph has appeared in the frame of the series published by Arnold Weissberger "The Chemistry of Heterocyclic Components", Interscience Publishers. The 2,6-dihydroxypyridine derivatives of formula II, according to Bobbitt and Scola, ibid., are converted by means of phosphoroxychloride or analogously by means of phosphoroxybromide at 180°C. into the corresponding 2,6-dichloro or 2,6-dibromopyridine derivatives of formula III:

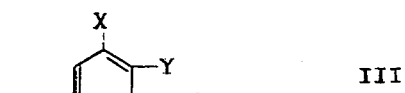

wherein X and Y have the above-stated meanings and Hal is bromine or preferably chlorine.

For the preparation of compounds of formula I, wherein $Z_2$ stands for chlorine or bromine and to which formula Ia then pertains, a compound of formula III is reacted with a compound of formula IV in accordance with the reaction:

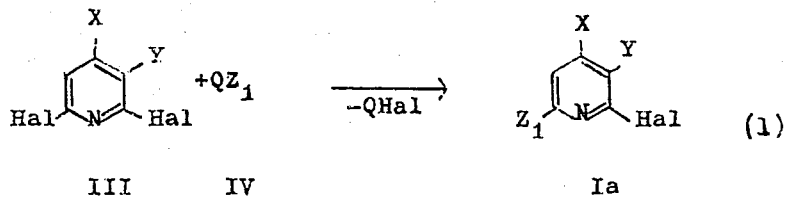

Q in this instance is hydrogen or a metal, preferably an alkali metal such as sodium or potassium. In the event that $Z_1$ stands for $-SO_2R_{12}$, zinc is especially preferred.

Reaction (1) is carried out in equimolar ratio at temperatures of 20°–100°C. in a suitable inert solvent. The exchange of the chlorine or bromine atom in the 6-position is ascertained by analysis of the NMR absorption of the obtained compounds of formula Ia.

preferred. In reaction equation (1), formula IV then stands for the compounds NaCN, KCN and $Zn(SO_2R_{12})_2$. In this instance, the reaction in accordance with reaction equation (1) is carried out preferably in the temperature range of 60°–80°C. in a suitable organic solvent such as an alcohol, ether, ester, carboxylic acid amide, N-substituted carboxylic acid amide such as dimethylformamide, dialkylsulfoxide such as dimethylsulfoxide or dialkylsulfone, all of these preferably having not more than 6 carbon atoms. In the reaction of sulfinates, the addition of a copper-I-salt is advantageous.

To the extent that in formula IV, $Z_1$ stands for the radicals $-OR_{12}$ or $-SR_{12}$, a metal atom is selected for Q, preferably an alkali metal atom such as sodium or potassium. In reaction equation (1), formula IV then stands for the compounds $NaOR_{12}$, $NaSR_{12}$, $KOR_{12}$ and $KSR_{12}$. In this instance, the reaction is conducted in accordance with reaction equation (1), preferably in the temperature range of 60°–100°C., in an inert organic solvent, e.g., an aromatic hydrocarbon such as benzene, toluene or xylene, or in an excess of the reaction constituent $HOR_{12}$ or $HSR_{12}$ as the solvent.

The compounds of formula Ia may be further reacted in accordance with the reaction:

To the extent that in formula IV, $Z_1$ stands for the radicals:

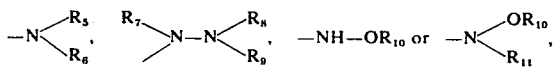

hydrogen is appropriately selected for Q, i.e., in the reaction equation (1) formula IV then stands for the compounds

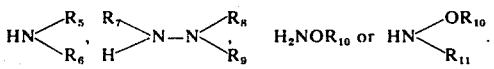

In this instance, the reaction is carried out in accordance with reaction equation (1), preferably in the temperature range of 20° to 50°C. and as suitable inert solvents, alkanols with a chain length of 1 to 4 carbon atoms are preferably used. In those instances where the physical properties are appropriate, an excess of one of the reaction constituents may also serve as the solvent.

To the extent that in formula IV, $Z_1$ stands for cyano or for $-SO_2R_{12}$, a metal is appropriately selected for Q, preferably an alkali metal such as sodium or potassium and in the event that $Z_1$ is $SO_2R_{12}$, zinc is particularly This reaction is carried out at temperatures of 20°–200°C. in a suitable solvent. The molar ratio of reactants is 1:1.

When $Z_2$ is OH in the compound of formula V, there is used a suitable alkali metal hydroxide such as sodium hydroxide or potassium hydroxide in an aqueous or aqueous-alcoholic medium. However, sodium carbonate, potassium hydroxide or similar compounds which release hydroxyl ions in an aqueous medium may also be used. The solvents may be alkanols having 1 to 4 carbon atoms. The preferred temperature range is 70°–150°C.

If $Z_2$ is $-SH$ in the compound of formula V, an alkali metal hydrosulfide, preferably NaSH or KSH, is used and the reaction is carried out in an aqueous medium, preferably at temperatures of 100°–150°C.

In the event $Z_2$ stands for $-OR_{12}$ or $-SR_{12}$, an alkali metal, preferably sodium or potassium, is selected for Q in formula V and the reaction constituents are reacted at temperatures of 60°–150°C., preferably at 60°–100°C., in a suitable inert solvent, e.g., an aromatic hydrocarbon such as benzene, toluene or xylene, or in an excess of the reaction constituent $HOR_{12}$ or $HSR_{12}$ as solvent.

In the event $Z_2$ is cyano or $-SO_2R_{12}$ in formula V, a metal is selected for Q, preferably an alkali metal such as sodium or potassium or when $Z_2$ is $-SO_2R_{12}$, zinc is also useful. The reaction between these compounds of formulae Ia and V is carried out in a suitable organic solvent at temperatures of 20°–100°C. and preferably 60°–80°C. Suitable organic solvents, for example, include alcohols, ethers, esters, carboxylic acid amides, N-substituted carboxylic acid amides such as dimethylformamide, dialkylsulfoxides such as dimethylsulfoxide or dialkylsulfones, all having preferably not more than 6 carbon atoms. In the use of sulfinates, the addition of a copper-I-salt is advantageous.

In the event $Z_2$ is

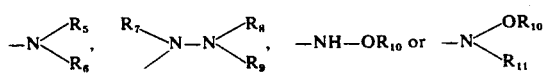

in formula V, hydrogen is selected for Q, and the constituents are reacted at 100°–200°C., preferably at 160°–180°C., in an inert solvent, preferably an alkanol having 1 to 4 carbon atoms or, in those instances where the physical properties are appropriate, an excess of one of the reaction constituents may be used as the solvent.

Novel compounds wherein $Z_2$ has the same meaning as $Z_1$ may be prepared in accordance with the reaction:

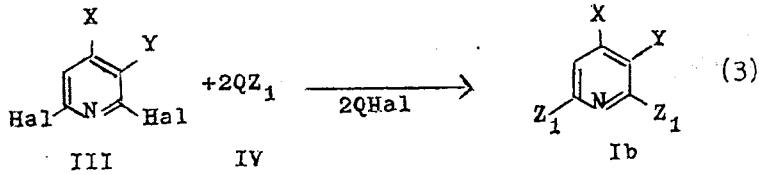

wherein a compound of formula III is reacted with a compound of formula IV in a molar ratio of at least 1:2 in a suitable solvent at temperatures of 20° to 200°C. When $Z_1$ is

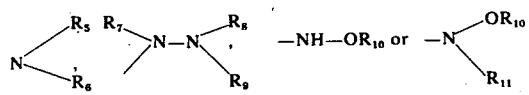

in formula IV, hydrogen is selected for Q, and when $Z_1$ is $-CN$, $-OR_{12}$, $-SR_{12}$ or $-SO_2R_{12}$, a metal is selected for Q, preferably an alkali metal such as sodium or potassium. Also when $Z_1$ is $-SO_2R_{12}$, zinc is suitable. Suitable solvents are alcohols, ethers, hydrocarbons etc. The selection of the solvent may be the same as described for reaction (1).

Novel compounds when $Z_2$ is $-OH$ may also be prepared by the reaction of a 2-hydroxy-6-bromo- or 2-hydroxy-6-chloropyridine derivative of formula VI with a compound of formula IV in a molar ratio of 1:1 in accordance with reaction:

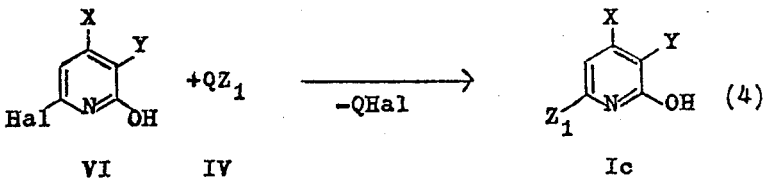

The reaction is carried out in a suitable solvent at temperatures of 20° to 100°C. The data respecting the solvents and the meaning and selection of Q set forth above for reaction equations (1) and (3), apply to reaction (4).

Compounds of formula VI may be prepared by the reaction of the corresponding 2,6-dihydroxypyridine compounds with phosphoroxychloride or phosphoroxybromide at 80°–100°C. in an inert organic solvent such as benzene, toluene or xylene.

If reactions (1) through (4) are carried out at temperatures which are above the boiling point of a reaction constituent or of the solvent used, then the utilization of excess pressure is required.

Compounds of formulae Ia, Ib and Ic are preferred groups of novel compounds. Further preferred compounds are those wherein in formula I:

X is alkyl having 1 to 3 carbon atoms, preferably methyl,

Y is cyano, $Z_1$ is cyano, alkoxy having 1 to 2 carbon atoms, alkylsulfonyl having 1 to 2 carbon atoms, amino, monoalkylamino having 1 to 3 carbon atoms or monoalkylamino having 1 to 3 carbon atoms and substituted by alkoxy having 1 to 2 carbon atoms and $Z_2$ is cyano, hydroxyl, alkoxy having 1 to 2 carbon atoms, alkylsulfonyl having 1 to 2 carbon atoms, amino, monoalkylamino having 1 to 3 carbon atoms or monoalkylamino having 1 to 3 carbon atoms and substituted by alkoxy having 1 to 2 carbon atoms.

Such preferred compounds are especially the pyridine compounds of the formulae:

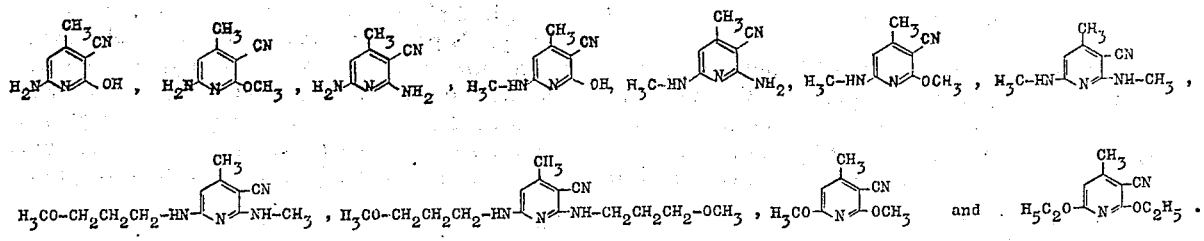

It is possible that the novel compounds of formula I in part exist in tautomeric forms. For example, the following tautomeric formulae are possible.

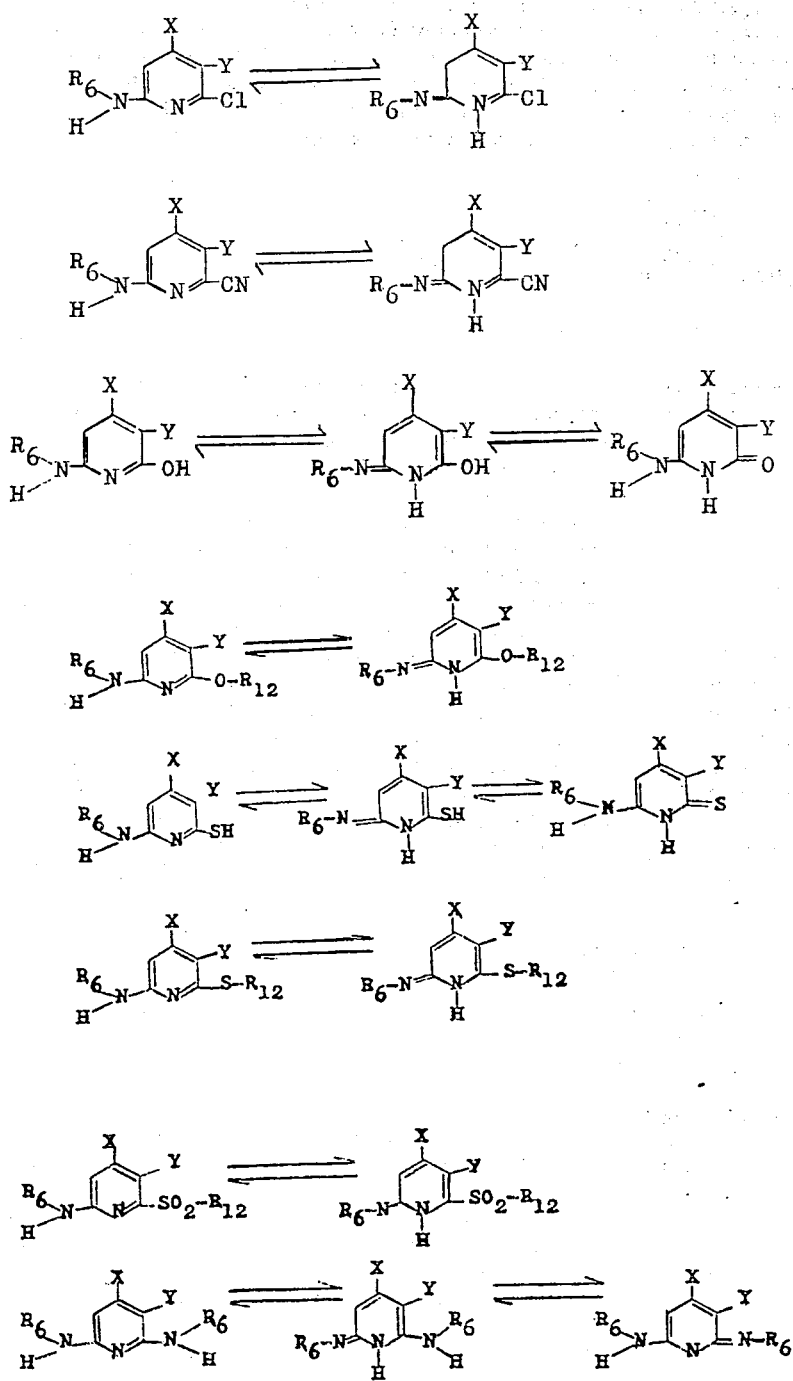

As used herein, formula I is also understood to embrace such possible tautomers.

As the reaction constituents of formula III such as 2,6-dichloro or 2,6-dibromo pyridine derivatives are suitable, for example, which in the X position contain hydrogen or a methyl, ethyl, n-propyl, isopropyl, vinyl, α-methylvinyl, n-butyl, isobutyl, sec.-butyl, n-amyl or isoamyl, n-hexyl, 2-dimethylaminoethyl, 2-diethylaminoethyl, 2-morpholinoethyl, 2-piperidinoethyl, 2-pyrrolidinoethyl, N-methyl-N'-piperazinoethyl, 2-cyanoethyl, 2-hydroxyethyl, 2-methoxyethyl, 2-acetoxyethyl, 2-phenoxyacetoxyethyl, N-ethylcarbamoyloxyethyl, N-phenylcarbamoyloxyethyl, 2-phenoxyethyl, 3-methoxypropyl, cyclohexyl, benzyl, 3-methylbenzyl, phenyl, 2-methylphenyl, 4-methylphenyl, 2,4-dimethylphenyl, 2-chloro-4-methylphenyl, 2-chlorophenyl, 4-chlorophenyl, 2-methoxyphenyl, 4-methoxyphenyl, 2,5-dimethyl-4-chlorophenyl or the following radicals:

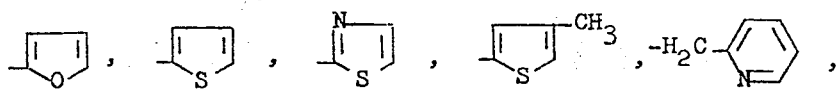

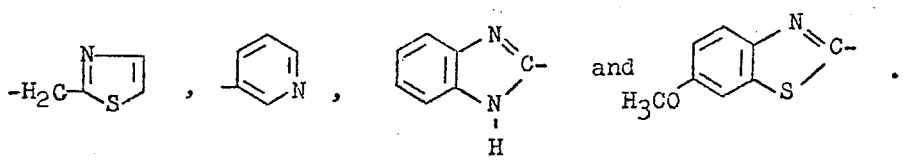

The compounds of formula III may, in the Y position, contain for example hydrogen, cyano, amino, nitroso, nitro, methyl, ethyl, 2-hydroxyethyl, 2-cyanoethyl, 2-acetoxyethyl, 2-benzoyloxyethyl, 2-methoxyethyl, 2-phenoxyethyl, 2-monoethylaminoethyl, 2-monomethylaminoethyl, 2-dimethylaminoethyl, 2-diethylaminoethyl, 2-morpholinoethyl, 2-piperidinoethyl, 2-pyrrolidinoethyl, n-propyl, isopropyl, vinyl, α-methylvinyl, n-butyl, isobutyl, sec.-butyl, n-amyl, isoamyl, n-hexyl, cyclohexyl, benzyl, phenyl, methoxycarbonyl, ethoxycarbonyl, n-propyloxycarbonyl, isopropyloxycarbonyl, n-butyloxycarbonyl, isobutyloxycarbonyl, sec.-butyloxycarbonyl, n-amyloxycarbonyl, n-isoamyloxycarbonyl, n-hexyloxycarbonyl, acetyl, acryloyl, propionyl, capronyl, capryl, hexahydrobenzoyl, phenacetyl, benzoyl, 4-methylbenzoyl, 2,4-dimethylbenzoyl, 4-methoxybenzoyl, 4-chlorbenzoyl, aminocarbonyl, monomethylaminocarbonyl, dimethylaminocarbonyl, ethyleniminocarbonyl, monoethylaminocarbonyl, monoisopropylaminocarbonyl, diethylaminocarbonyl, monooxethylaminocarbonyl, mono-γ-methoxypropylaminocarbonyl, morpholinocarbonyl, piperidinocarbonyl, cyclohexylaminocarbonyl, benzylaminocarbonyl, anilinocarbonyl, 4-methylanilinocarbonyl, N-methylanilinocarbonyl, methylsulfonyl, ethylsulfonyl, n-propylsulfonyl, isopropylsulfonyl, n-butylsulfonyl, isobutylsulfonyl, sec.-butylsulfonyl, n-amylsulfonyl, isoamylsulfonyl, n-hexylsulfonyl, benzylsulfonyl, phenylsulfonyl, 4-methylphenylsulfonyl, 2,4-dimethylphenylsulfonyl, 4-methoxyphenylsulfonyl, 4-chlorphenylsulfonyl, aminosulfonyl, monomethylaminosulfonyl, dimethylaminosulfonyl, ethyleniminosulfonyl, monoethylaminosulfonyl, monoisopropylaminosulfonyl, diethylaminosulfonyl, monooxethylaminosulfonyl, mono-γ-methoxypropylaminosulfonyl, morpholinosulfonyl, piperidinosulfonyl, cyclohexylaminosulfonyl, benzylaminosulfonyl, anilinosulfonyl, 4-methylanilinosulfonyl, N-methylanilinosulfonyl or the radicals

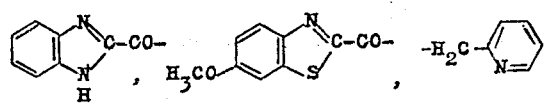

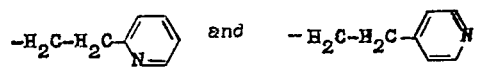

Of course, suitable starting compounds of formula III are also such 2,6-dichloro or 2,6-dibromopyridine derivatives which are identically substituted in the X and Y position, the preferred substituents being those which were indicated above for the X position.

Suitable reaction constituents

of formulae IV and V include, for example, the following primary and secondary amines and diamines:

Primary Amines ammonia, methylamine, ethylamine, 2-hydroxyethylamine, 2-methoxyethylamine, 3-phenoxyethylamine, 3-cyanoethylamine, n-propylamine, isopropylamine, 3-hydroxypropylamine-(1), 3-methoxypropylamine-(1), 3-isopropoxypropylamine-(1), 3-cyanopropylamine-(1), allylamine, 1-methallylamine, 2-methallylamine, n-butylamine, isobutylamine, sec.-butylamine, tert.-butylamine, 2-amino-2-methylpropanol-(1), crotylamine, 3-aminopentane, n-amylamine, isoamylamine, n-hexylamine, cyclohexylamine, benzylamine, 2-phenylethylamine, aniline, 4-methylaniline, 4-methoxyaniline, 2,4-dimethylaniline, 1-aminonaphthaline, 2-aminonaphthaline,

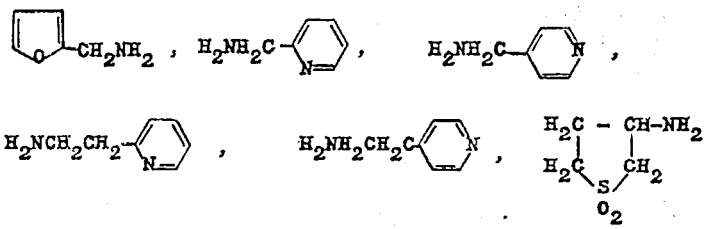

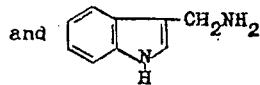

Secondary Amines dimethylamine, diethylamine, N-(2-cyanoethyl)-N-(2-hydroxyethyl)-amine, N-di-(2-hydroxyethyl)-amine, N-di-(2-cyanoethyl)-amine, N-methyl-(2-hydroxyethyl)-amine, N-isopropyl-(2-hydroxyethyl)-amine, N-n-butyl-(2-hydroxyethyl)-amine, N-cyclohexyl-(2-hydroxyethyl)-amine, N-benzyl-(2-hydroxyethyl)-amine, di-n-propylamine, di-isopropylamine, di-n-butylamine, di-isobutylamine, di-n-amylamine, di-n-hexylamine, morpholine, pyrrolidine, piperidine, N-methylpiperazine, N-methylcyclohexylamine, N-ethylcyclohexylamine, N-methylbenzylamine, N-methyl-3-methylbenzylamine, N-methylaniline, N-ethylaniline, N-2-hydroxyethylaniline, N-benzylaniline, N-methyl-2-chloraniline and N-ethyl-2-chloraniline.

Diamines

N-methyl-N',N'-dimethylhydrazine, N,N-dimethylhydrazine, N,N-diethylhydrazine, N-methyl-N-phenylhydrazine, N-aminopyrrolidine, N-aminopiperidine, N-aminopiperazine, N-aminomorpholine, N,N-dimethylethylenediamine, N,N-diethylethylenediamine, N,N-dimethylpropylenediamine-(1,3), or N,N-diethylpropylenediamine-(1,3), 2-morpholinoethylamine, 2-piperidinoethylamine, 2-pyrrolidinoethylamine and N-methyl-N'-3-amino-n-propylpiperazine of the formula:

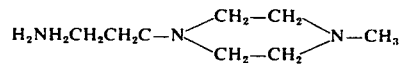

Suitable reaction constituents $H_2NOR_{10}$ or

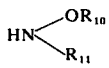

according to the general formulae IV and V, for example, are:

Hydroxylamines

  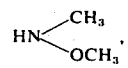  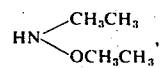  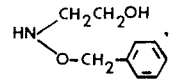

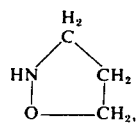  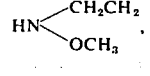  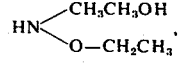  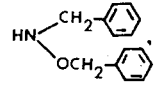

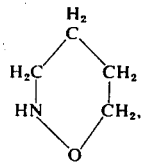  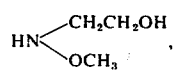  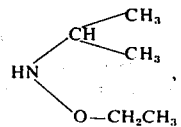

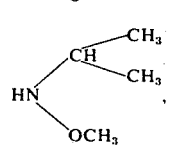  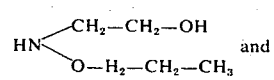 and  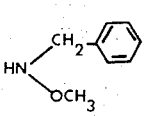

As the hetarylamines for $Z_1$ and $Z_2$, the following may, for example, be used:
3-aminodiphenylene oxide
3-aminodiphenylene sulfide
3-aminodiphenylene sulfone
2-aminocarbazole
3-amino-N-methylcarbazole
3-amino-N-ethylcarbazole
3-amino-N-$\beta$-hydroxyethylcarbazole
3-amino-N-$\beta$-cyanoethylcarbazole
3-amino-N-n-propylcarbazole
3-amino-N-isopropylcarbazole
3-amino-N-($\beta$-dimethylaminoethyl)-carbazole
3-amino-N-($\beta$-diethylaminoethyl)-carbazole
3-amino-N-($\gamma$-dimethylaminopropyl)-carbazole
3-amino-N-($\alpha$-methyl-$\beta$-dimethylaminoethyl)-carbazole As the compounds HO-$R_{12}$ or HS-$R_{12}$, which after their conversion into the corresponding metal compounds, particularly the corresponding alkali metal compounds (especially the corresponding sodium and potassium compounds) are suitable as reaction constituents of formulae IV and V, the following alcohols, phenols or the corresponding mercaptans and thiophenols may be utilized: methanol, ethanol, 2-cyanomethanol-(1), ethylene glycol monomethyl ether, ethylene glycol monoethylether, ethylene glycol monoisopropyl ether, ethylene glycol mono-n-butylether, ethylene glycol monophenyl ether, ethylene glycol monoxylenyl ether, diethylene glycol monomethylether, diethylene glycol monoethylether, diethylene glycol mono-n-butylether, triethylene glycol monomethylether, triethylene glycol monoethylether, triethylene glycol mono-n-butylether, n-propanol, isopropanol, propene-(1)-ol-(3), 2-methylpropene-(1)-ol-(3), n-butanol, sec.-butanol, isobutanol, tert.-butanol, 3-methoxybutanol-(1), 4-methoxybutanol-(1), butene-(1)-ol-(2), n-pentanol, isopentanol, n-hexanol, cyclohexanol, 4-methylcyclohexanol, 4-methoxycyclohexanol, phenylmethanol, (4-chlorophenyl)-methanol, phenylethanol, (4-cyanophenyl)-ethanol, phenol, 2-methylphenol, 3-methylphenol, 4-methylphenol, 2,3-dimethylphenol, 2,4-dimethylphenol, 2,5-dimethylphenol, 2,6-dimethylphenol, 3,4-dimethylphenol, 3,5-dimethylphenol, 2-methoxyphenol, 3-methoxyphenol, 4-methoxyphenol, 2-methoxy-3-methylphenol, 2-methoxy-4-methylphenol, 2-methoxy-5-methylphenol, 2-methoxy-6-methylphenol, 3-methoxy-5-methylphenol, 3-methoxy-6-methylphenol, 4-methoxy-5-methylphenol, 4-methoxy-6-methylphenol, 2,3-dimethoxyphenol, 2,4-dimethoxyphenol, 3,5-dimethoxyphenol, 2-chlorophenol, 3-chlorophenol, 4-chlorophenol, 2-bromophenol, 3-bromophenol, 4-bromophenol, 2-cyanophenol, 3-cyanophenol, 4-cyanophenol, 2,3-dichlorophenol, 2,4-dichlorophenol, 2,5-dichlorophenol, 2,6-dichlorophenol, 3,4-dichlorophenol, 3,5-dichlorophenol, 2,3-dibromophenol, 2,4-dibromophenol, 2,5-dibromophenol, 2,6-dibromophenol, 3,4-dibromophenol, 3,5-dibromophenol, 2-methyl-3-chlorophenol, 2-methyl-4-chlorophenol, 2-methyl-5-chlorophenol, 2-methyl-6-chlorophenol, 2-methyl-3-bromophenol, 2-methyl-4-bromophenol, 2-methyl-5-bromophenol, 2-methyl-6-bromophenol, 3-methyl-2-chlorophenol, 3-methyl-4-chlorophenol, 3-methyl-6-chlorophenol, 3-methyl-2-bromophenol, 3-methyl-4-bromophenol, 3-methyl-6-bromophenol, 4-methyl-5-chlorophenol, 4-methyl-6-chlorophenol, 4-methyl-5-bromophenol, 4-methyl-6-bromophenol, 4-chloropyrocatechol-1-methylether, 5-chloropyrocatechol-1-methylether, 4-bromopyrocatechol-1-methylether, 5-bromopyrocatechol-1-methylether, 4-chloroesorcinol-1-methylether, 4-chlororesorcinol-3-methylether, 4-bromoresorcinol-1-methylether, 4-bromoresorcinol-3-methylether, 2-chlorohydroquinone-1-methylether, 2-chlorohydroquinone-2-methylether, 5-chlororesorcinol-1-methylether, 1-naphthol, 2-naphthol, 2-methyl-1-naphthol, 3-methyl-1-naphthol, 4-methyl-1-naphthol, 7-methyl-1-naphthol, 3,6-dimethyl-1-naphthol, 3,7-dimethyl-1-naphthol, 4,6-dimethyl-1-naphthol, 4,7-dimethyl-1-naphthol, 6,7-dimethyl-1-naphthol, 4-methoxy-1-naphthol, 5-methoxy-1-naphthol, 6-methoxy-1-naphthol, 7-methoxy-1-naphthol, 8-methoxy-1-naphthol, 2-chloro-1-naphthol, 3-chloro-1-naphthol, 4-chloro-1-naphthol, 5-chloro-1-naphthol, 7-chloro-1-naphthol, 8-chloro-1-naphthol, 2,3-dichloro-1-naphthol, 2,4-dichloro-1-naphthol, 5,7-dichloro-1-naphthol, 5,8-dichloro-1-naphthol, 2-chloro-4-bromo-1-naphthol, 2-bromo-1-naphthol, 3-bromo-1-naphthol, 4-bromo-1-naphthol, 5-bromo-1-naphthol, 6-bromo-1-naphthol, 7-bromo-1-naphthol, 8-bromo-1-naphthol, 2-ethyl-4-bromo-1-naphthol, 2,4-dibromo-1-naphthol, 1-methyl-2-naphthol, 6-methyl-2-naphthol, 1,4-dimethyl-2-naphthol, 3,6-dimethyl-2-naphthol, 3,7-dimethyl-2-naphthol, 6,7-dimethyl-2-naphthol, 1-chloro-2-naphthol, 3-chloro-2-naphthol, 4-chloro-2-naphthol, 5-chloro-2-naphthol, 6-chloro-2-naphthol, 7-chloro-2-naphthol, 8-chloro-2-naphthol, 1,3-dichloro-2-naphthol, 1,4-dichloro-2-naphthol, 1-bromo-2-naphthol, 3-bromo-2-naphthol, 4-bromo-2-naphthol, 5-bromo-2-naphthol, 6-bromo-2-naphthol, 7-bromo-2-naphthol, 8-bromo-2-naphthol, 1-methyl-6-bromo-2-naphthol, 1-ethyl-6-bromo-2-naphthol, 1,6-dibromo-2-naphthol, 3,6-dibromo-2-naphthol, 3,7-dibromo-2-naphthol and 4,6-dibromo-2-naphthol.

For the preparation of the novel compounds of formula I, wherein the substituent $Z_1$ and/or $Z_2$ signifies a $-SO_2-R_{12}$ radical, sulfinates are employed, preferably zinc sulfinates of the formula $Zn\ (SO_2-R_{12})_2$. They allow the introduction of, for example, the following radicals: methylsulfonyl, chloromethylsulfonyl, ethylsulfonyl, 2-chloroethylsulfonyl, n-propylsulfonyl, isopropylsulfonyl, n-butylsulfonyl, isobutylsulfonyl, sec.-butylsulfonyl, n-amylsulfonyl, isoamylsulfonyl, n-hexylsulfonyl, cyclohexylsulfonyl, benzylsulfonyl, phenylsulfonyl, 2,4-dimethylphenylsulfonyl, 4-methylphenylsulfonyl, 4-methoxyphenylsulfonyl, 4-chlorophenylsulfonyl, 4-chloro-3-methylphenylsulfonyl and 4-bromophenylsulfonyl.

The compounds of the present invention are valuable intermediates, in particular for the preparation of dyestuffs, preferably of azo dyestuffs. As far as these azo dyes do not contain ionogenic groups, they may be employed as disperse dyes for dyeing and printing synthetic hydrophobic fiber material, whereas those azo dyes which do contain ionogenic groups are suited for dyeing and printing cotton, wool, silk, polyamide and modified polyacrylonitrile.

Moreover, the compounds of the present invention are valuable pest control agents — in particular if they are employed as insectizides — , as well as valuable pharmaceuticals — above all if they are employed as analeptics, analgetics and diuretics.

Azo dyes containing the compounds of the present invention may be prepared, for instance, by diazotizing a diazotizable aromatic amine and coupling it with a compound of the present invention. The diazotization and the coupling are carried out in the usual manner. According to the respective initial products employed, this working method leads to the preparation, for instance, of disperse dyes, reactive dyes, cationic dyes or acid dyes. All of these azo dyes exhibit outstanding tinctorial properties, in particular a high coloring strength and a very good fastness to light, perspiration, water, sea water, alkalies and to washing. The disperse dyes distinguish themselves above all by an excellent fastness to dry-heat pleating and setting, ozone, waste-gas fading and to rubbing, by a high resistance when subjected to various permanent press treatments and by a good covering power even when applied onto textured polyester materials. The reactive dyes distinguish themselves in particular by an even color depth obtained in the different setting processes. The azo dyes mentioned hereinbefore are suited for dyeing and printing textile materials according to various known processes. The preparation of the dyes as well as their application for dyeing and printing are described in Examples 15 – 19.

In the following examples, "p.b.w." means parts by weight.

EXAMPLE 1

To a composition of 320 p.b.w. ethyl alcohol and 83.7 p.b.w. 2,6-dichloro-3-cyano-4-methylpyridine, which are placed in an autoclave, there are added 51.0 p.b.w. liquid ammonia and subsequently the reaction liquid is heated for 18 hours at 200°C. After cooling, the ethyl alcohol is then distilled off, the residue agitated with 300 p.b.w. water, drawn off, washed with water and dried. The resulting 2,6-diamino-3-cyano-4-methylpyridine having the formula

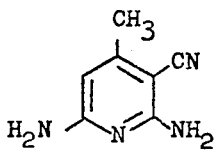

may be purified by crystallization from ethyl alcohol.
Analysis: $C_7H_8N_4$ Calculated: 37.8% N Found: 37.4% N.

EXAMPLE 2

A solution of 400 p.b.w. ethyl alcohol, 93.0 p.b.w. 2,6-dichloro-3-cyano-4-methylpyridine and 274.0 p.b.w. diethylamine is agitated 24 hours at 50°C. Upon cooling of the reaction solution, the resulting 2-chloro-3-cyano-4-methyl-6-diethylaminopyridine of the formula

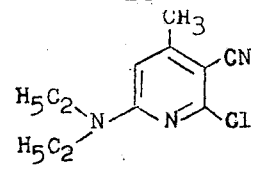

EXAMPLE 3

The mixture of Example 2 is agitated in an autoclave for 12 hours at 150°C. Upon cooling, the ethyl alcohol is then distilled off and the residue agitated with 50 p.b.w. water and 245 p.b.w. soda lye, 33° Be. The resulting 2,6-bis-(diethylamino)-3-cyano-4-methylpyridine of the formula

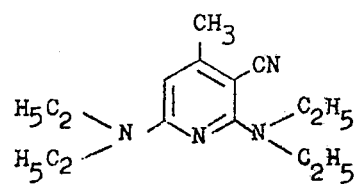

is an oil which is isolated with ether. It may be purified by vacuum distillation.
Analysis: $C_{15}H_{24}N_4$ Calculated: 21.5% N. Found: 21.5% N. is drawn off and washed with water. It may be purified by recrystallization from ethyl alcohol.
Analysis: $C_{10}H_{12}ClN_3$ Calculated: 20.1% N 16.7% Cl. Found: 20.3% N 17.0% Cl.

EXAMPLE 4

Introduced into 200 p.b.w. methyl alcohol while cooling were 3.7 p.b.w. sodium. Added to this sodium methyl solution then were 33.5 p.b.w. 2-chloro-3-cyano-4-methyl-6-diethylaminopyridine and subsequently the reaction solution was heated to the point of boiling for 24 hours. Then the methyl alcohol was distilled off, the residue taken up with 100 p.b.w. water, drawn off, washed with water and dried. The resulting 2-methoxy-3-cyano-4-methyl-6-diethylaminopyridine of the formula

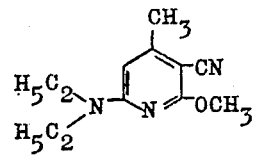

may be purified by recrystallization from methanol.
Analysis: $C_{12}H_{17}N_3O$ Calculated: 19.2 % N 14.2 % —OCH$_3$. Found: 19.0 % N 13.8 % —OCH$_3$.

EXAMPLE 5

A composition consisting of 432 p.b.w. n-propylamine and 187 p.b.w. 2,6-dichloro-3-cyano-4-methylpyridine is agitated in an autoclave for 2 hours at 100°C. Upon cooling, the reaction liquor is decomposed in water, the resulting 2-chloro-3-cyano-4-methyl-6-n-propylaminopyridine having the formula

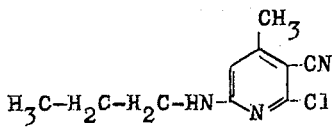

is crystallized out. The pyridine derivative is then drawn off and washed on the suction apparatus first with 100 p.b.w. ethyl alcohol and subsequently with 500 p.b.w. water. The substance is analytically pure. Its constitution, i.e., the exchange of the 6-position halogen atom in the 2,6-dichloro-3-cyano-4-methylpyridine against the diethylamino group was assured by MNR absorption analysis.

Analysis: $C_{11}H_{14}ClN_3$ Calculated: 18.8% N 15.7% Cl. Found: 18.5% 15.7% Cl.

EXAMPLE 6

A composition of 100 p.b.w. 3-dimethylaminopropylamine(1) and 41.8 p.b.w. 2-chloro-3-cyano-4-methyl-6-n-propylaminopyridine are agitated for 2 hours at 140°C. The reaction melt upon cooling is stirred with water, the residue is drawn off and washed with water. The resulting 2-(3'-dimethylamino-n-propylamino)-3-cyano-4-methyl-6-n-propylaminopyridine having the formula

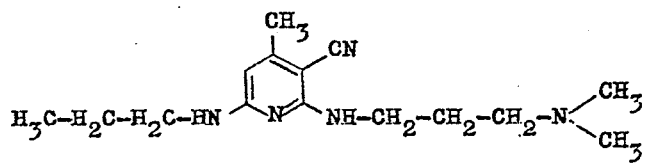

may be purified by crystallization from ethyl alcohol.

Analysis: $C_{15}H_{25}N_5$ Calculated: 25.4% N. Found: 25.2% N.

EXAMPLE 7

Introduced into a solution of 155 p.b.w. monomethylamine in 1000 p.b.w. isopropylalcohol are 187 p.b.w. 2,6-dichloro-3-cyano-4-methylpyridine. Subsequently, the reaction solution is heated in an autoclave for 5 hours at 200°C. Upon cooling to room temperature, the resulting 2,6-bis-(monomethylamino)-3-cyano-4-methylpyridine having the formula

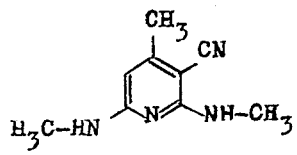

is drawn off, first washed with isopropyl alcohol, then with water and dried. It may be purified by crystallization from isopropyl alcohol.

Analysis: $C_9H_{12}N_4$ Calculated: 31.8% N. Found: 32.0% N.

EXAMPLE 8

A composition of 200 p.b.w. ethyl alcohol, 83.7 p.b.w. 2,6-dichloro-3-cyano-4-methylpyridine and 180 p.b.w. 3-methoxypropylamine-(1) is heated in an autoclave for 18 hours at 180°C. Upon cooling, the ethyl alcohol is distilled off, the residue is stirred with 100 p.b.w. water with the addition of 150 p.b.w. soda lye, 33°Be, drawn off, washed with water and dried. The resulting 2,6-bis-(3'-methoxy-n-propylamino)-3-cyano-4-methylpyridine having the formula

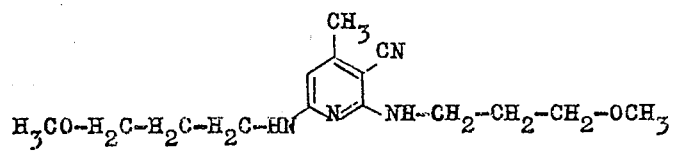

may be purified by vacuum distillation.

Analysis: $C_{15}H_{24}N_4O_2$ Calculated: 19.2% N. Found: 19.6% N.

EXAMPLE 9

A composition consisting of 100 p.b.w. morpholine and 37.4 p.b.w. 2,6-dichloro-3-cyano-4-methylpyridine is heated for 30 minutes at 130°C. The reaction melt is then decomposed on ice, the residue is drawn off, washed with water, and dried. The resulting 2,6-bis-(morpholino)-3-cyano-4-methylpyridine having the formula

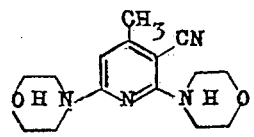

may be purified by crystallization from ethyl alcohol.

Analysis: $C_{15}H_{20}N_4O_2$ Calculated: 19.4% N. Found: 19.7% N.

EXAMPLE 10

There are introduced 37.2 p.b.w. 2,6-dichloro-3-cyano-4-methylpyridine into 150.0 p.b.w. aniline. This reaction solution is then heated for 24 hours at 150°C. and subsequently decomposed in 1000 p.b.w ice with the addition of 350 p.b.w. crude hydrochloric acid (D = 1.153). The resulting 2,6-bis-(anilino)-3-cyano-4-methylpyridine having the formula

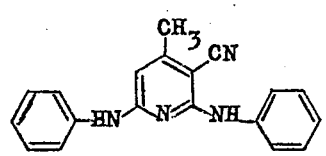

may be purified by crystallization from ethyl alcohol.

Analysis: $C_{19}H_{16}N_4$ Calculated: 18.7% N. Found: 18.5% N.

EXAMPLE 11

Introduced into 80 p.b.w. methyl alcohol are 7.6 p.b.w. sodium during cooling, then there are added 27.9 p.b.w. 2,6-dichloro-3-cyano-4-methylpyridine to this sodium methylate solution and subsequently the reaction solution is heated to the point of boiling for 24 hours. Then the methyl alcohol is distilled off. The residue is taken up with 100 p.b.w. water, drawn off, washed with water and dried. The resulting 2,6-dimethoxy-3-cyano-4-methylpyridine having the formula

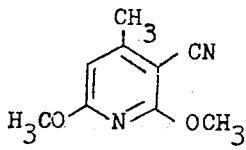

may be purified by recrystallization from methyl alcohol.

Analysis: $C_9H_{10}N_2O_2$. Calculated: 15.7% N 34.8% —$OCH_3$. Found: 15.5% N 34.2% —$OCH_3$.

EXAMPLE 12

There are introduced 27.9 p.b.w. of 2,6-dichloro-3-cyano-4-methylpyridine into a sodium ethylate solution, which had been prepared from 80 p.b.w. ethyl alcohol and 3.8 p.b.w. sodium. Subsequently, the reaction solution is heated to the point of boiling for 24 hours. The ethyl alcohol is then distilled off, the residue is stirred with 100 p.b.w. water, and the resulting 2-chloro-3-cyano-4-methyl-4-ethoxypyridine having the formula

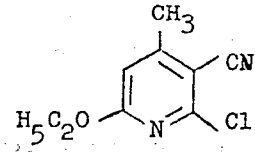

is taken up with ether. It may be purified by vacuum distillation.

Analysis: $C_9H_9ClN_2O$. Calculated: 14.3% N 17.8% Cl. Found: 14.5% N 17.6% Cl.

In the following table there are presented further pyridine compounds prepared in accordance with the herein described process:

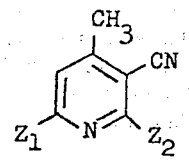

or tautomeric formulae.

| No. | $Z_1$ | $Z_2$ | Empirical Formula | Cal'd. N% | Found N% |
|---|---|---|---|---|---|
| 1. | —$NHCH_2CH_3$ | —$NHCH_2CH_3$ | $C_{11}H_{16}N_4$ | 27.5 | 27.5 |
| 2. | —$NHCH_2CH_2OH$ | —$NHCH_2CH_2OH$ | $C_{11}H_{16}N_4O_2$ | 23.7 | 24.0 |
| 3. | —$NHCH_2CH_2OCH_3$ | —$NHCH_2CH_2OCH_3$ | $C_{13}H_{20}N_4O_2$ | 21.2 | 21.0 |
| 4. | —$NHCH_2CH_2CN$ | —$NHCH_2CH_2CN$ | $C_{13}H_{14}N_6$ | 33.1 | 33.5 |
| 5. | —$NHCH_2CH_2CH_3$ | —$NHCH_2CH_2CH_3$ | $C_{13}H_{20}N_4$ | 24.1 | 24.6 |
| 6. | —NH—CH(CH$_3$)$_2$ | —NH—CH(CH$_3$)$_2$ | $C_{13}H_{20}N_4$ | 24.1 | 24.4 |
| 7. | —NH—$(CH_2)_2CH_2OCH_3$ | —NH—$(CH_2)_2CH_2OCH_3$ | $C_{15}H_{24}N_4O_2$ | 19.2 | 19.0 |
| 8. | —$NHCH_2CH=CH_2$ | —$NHCH_2CH=CH_2$ | $C_{13}H_{16}N_4$ | 24.6 | 24.2 |
| 9. | —NH—$C_4H_9(n)$ | —NH—$C_4H_9(n)$ | $C_{15}H_{24}N_4$ | 21.5 | 21.8 |
| 10. | —NH—$C_4H_9(sec)$ | —NH—$C_4H_9(sec)$ | $C_{15}H_{24}N_4$ | 21.5 | 21.3 |
| 11. | —NH—CH(CH$_2$—CH$_3$)$_2$ | —NH—CH(CH$_2$—CH$_3$)$_2$ | $C_{17}H_{28}N_4$ | 19.4 | 19.8 |
| 12. | —NH—$C_5H_{11}$(iso) | —NH—$C_5H_{11}$(iso) | $C_{17}H_{28}N_4$ | 19.4 | 19.6 |
| 13. | —NH—$C_6H_{13}(n)$ | —NH—$C_6H_{13}(n)$ | $C_{19}H_{34}N_4$ | 17.7 | 18.1 |
| 14. | —NH—cyclohexyl | —NH—cyclohexyl | $C_{19}H_{28}N_4$ | 17.9 | 17.5 |
| 15. | —NH—$CH_2$—phenyl | —NH—$CH_2$—phenyl | $C_{21}H_{20}N_4$ | 17.1 | 17.5 |
| 16. | —NH—$CH_2$—$CH_2$—phenyl | —NH—$CH_2$—$CH_2$—phenyl | $C_{23}H_{24}N_4$ | 15.7 | 15.5 |
| 17. | —NH—naphthyl | —NH—naphthyl | $C_{27}H_{20}N_4$ | 14.0 | 14.3 |
| 18. | isoxazolyl-CH$_2$—NH— (with CN) | isoxazolyl-CH$_2$—NH— | $C_{17}H_{16}N_4O_2$ | 18.2 | 18.5 |

-continued

| No. | $Z_1$ | $Z_2$ | Empirical Formula | Cal'd. N% | Found N% |
|---|---|---|---|---|---|
| 19. | 4-pyridyl-CH$_2$-NH- | 4-pyridyl-CH$_2$-NH- | $C_{19}H_{18}N_6$ | 25.5 | 25.7 |
| 20. | (tetrahydrothiophene-1,1-dioxide-3-yl)-NH- | (tetrahydrothiophene-1,1-dioxide-3-yl)-NH- | $C_{15}H_{20}N_4O_4S_2$ | 14.6 | 15.0 |
| 21. | (1H-indol-3-yl)-CH$_2$-NH- | (1H-indol-3-yl)-CH$_2$-NH- | $C_{25}H_{22}N_6$ | 20.7 | 21.0 |
| 22. | -N(CH$_3$)$_2$ | -N(CH$_3$)$_2$ | $C_{11}H_{16}N_4$ | 27.5 | 27.2 |
| 23. | -N(CH$_2$CH$_2$CN)$_2$ | -N(CH$_2$CH$_2$CN)$_2$ | $C_{19}H_{20}N_8$ | 31.1 | 36.7 |
| 24. | -N(CH$_2$CH$_2$CN)(CH$_2$CH$_2$OH) | -N(CH$_2$CH$_2$CN)(CH$_2$CH$_2$OH) | $C_{17}H_{22}N_6O_2$ | 26.3 | 26.8 |
| 25. | -N(CH$_3$)(CH$_2$CH$_2$OH) | -N(CH$_3$)(CH$_2$CH$_2$OH) | $C_{13}H_{20}N_4O_2$ | 21.2 | 21.6 |
| 26. | -N(C$_4$H$_9$(n))(CH$_2$CH$_2$OH) | -N(C$_4$H$_9$(n))(CH$_2$CH$_2$OH) | $C_{19}H_{32}N_4O_2$ | 16.1 | 16.5 |
| 27. | -N(cyclohexyl)(CH$_2$CH$_2$OH) | -N(cyclohexyl)(CH$_2$CH$_2$OH) | $C_{23}H_{36}N_4O_2$ | 14.0 | 14.6 |
| 28. | -N(CH$_2$C$_6$H$_5$)(CH$_2$CH$_2$OH) | -N(CH$_2$C$_6$H$_5$)(CH$_2$CH$_2$OH) | $C_{25}H_{28}N_4O_2$ | 13.5 | 13.2 |
| 29. | -N(C$_3$H$_7$(n))$_2$ | -N(C$_3$H$_7$(n))$_2$ | $C_{19}H_{32}N_4$ | 17.7 | 18.2 |
| 30. | -N(C$_4$H$_9$(n))$_2$ | -N(C$_4$H$_9$(n))$_2$ | $C_{23}H_{40}N_4$ | 15.1 | 15.5 |
| 31. | -N(C$_6$H$_{13}$(n))$_2$ | -N(C$_6$H$_{13}$(n))$_2$ | $C_{31}H_{56}N_4$ | 11.6 | 11.2 |
| 32. | morpholino | morpholino | $C_{15}H_{20}N_4O_2$ | 19.4 | 19.6 |
| 33. | piperidino | piperidino | $C_{17}H_{24}N_4$ | 19.7 | 19.3 |
| 34. | 4-methylpiperazino | 4-methylpiperazino | $C_{17}H_{26}N_6$ | 26.8 | 26.2 |
| 35. | 4-ethylpiperazino | 4-ethylpiperazino | $C_{19}H_{20}N_6$ | 24.6 | 25.1 |
| 36. | pyrrolidino | pyrrolidino | $C_{15}H_{20}N_4$ | 21.8 | 22.2 |
| 37. | -NH-N(CH$_3$)(C$_6$H$_5$) | -NH-N(CH$_3$)(C$_6$H$_5$) | $C_{21}H_{22}N_6$ | 23.5 | 23.8 |

-continued

| No. | Z₁ | Z₂ | Empirical Formula | Cal'd. N% | Found N% |
|---|---|---|---|---|---|
| 38. | −NH−N(CH₃)₂ | −NH−N(CH₃)₂ | $C_{11}H_{18}N_6$ | 35.9 | 35.6 |
| 39. | −N(CH₃)−N(CH₃)₂ | −N(CH₃)−N(CH₃)₂ | $C_{13}H_{22}N_6$ | 32.1 | 32.5 |
| 40. | −NH−N(C₂H₅)₂ | −NH−N(C₂H₅)₂ | $C_{15}H_{26}N_6$ | 29.0 | 29.4 |
| 41. | −NH−N(C₂H₅)(C₆H₅) | −NH−N(C₂H₅)(C₆H₅) | $C_{23}H_{26}N_6$ | 21.8 | 21.5 |
| 42. | −NH−N(morpholino) | −NH−N(morpholino) | $C_{15}H_{22}N_6O_2$ | 26.4 | 26.2 |
| 43. | −NHCH₂CH₂N(CH₃)₂ | −NHCH₂CH₂N(C₂H₅)₂ | $C_{17}H_{30}N_6$ | 26.4 | 26.0 |
| 44. | −NHCH₂CH₂N(C₂H₅)₂ | −NHCH₂CH₂N(C₂H₅)₂ | $C_{19}H_{34}N_6$ | 24.3 | 24.5 |
| 45. | −NHCH₂CH₂CH₂N(CH₃)₂ | −NHCH₂CH₂CH₂N(CH₃)₂ | $C_{17}H_{30}N_6$ | 26.4 | 26.1 |
| 46. | −NHCH₂CH₂CH₂−N(morpholino) | −NHCH₂CH₂CH₂−N(morpholino) | $C_{21}H_{34}N_6O_2$ | 20.9 | 20.7 |
| 47. | −NHCH₂CH₂CH₂−N(piperidino) | −NHCH₂CH₂CH₂−N(piperidino) | $C_{23}H_{38}N_6$ | 21.1 | 21.5 |
| 48. | −NH−OH | −NH−OH | $C_7H_8N_4O_2$ | 31.1 | 31.6 |
| 49. | −N(CH₃)(OCH₃) | −N(CH₃)(OCH₃) | $C_{11}H_{16}N_4O_2$ | 23.7 | 24.2 |
| 50. | −N(CH₂CH₂OH)(OCH₃) | −N(CH₂CH₂OH)(OCH₃) | $C_{13}H_{20}N_4O_4$ | 18.9 | 19.3 |
| 51. | −N(CH₂C₆H₅)(OCH₃) | −N(CH₂C₆H₅)(OCH₃) | $C_{23}H_{24}N_4O_2$ | 14.4 | 15.0 |
| 52. | −N(CH₂−CH₃)(O−CH₂−CH₃) | −N(CH₂−CH₃)(O−CH₂−CH₃) | $C_{15}H_{24}N_4O_2$ | 19.2 | 19.6 |
| 53. | −N(CH₂CH₂OH)(O−CH₂CH₂OH) | −N(CH₂CH₂OH)(O−CH₂CH₂OH) | $C_{15}H_{24}N_4O_6$ | 15.7 | 16.2 |
| 54. | −N(CH₂CH₂OH)(O−CH₂C₆H₅) | −N(CH₂CH₂OH)(O−CH₂C₆H₅) | $C_{25}H_{28}N_4O_4$ | 12.5 | 12.2 |
| 55. | isoxazolidinyl | isoxazolidinyl | $C_{13}H_{16}N_4O_2$ | 21.5 | 21.2 |
| 56. | 1,2-oxazinanyl | 1,2-oxazinanyl | $C_{15}H_{20}N_4O_2$ | 19.4 | 19.8 |

-continued

| No. | Z₁ | Z₂ | Empirical Formula | Cal'd. N% | Found N% |
|---|---|---|---|---|---|
| 57. | —NH₂ | —Cl | $C_7H_6ClN_3$ | 25.1 | 25.4 |
| 58. | —NH₂ | —CN | $C_8H_6N_4$ | 35.7 | 35.5 |
| 59. | ″ | —OH | $C_7H_7N_3O$ | 28.2 | 28.6 |
| 60. | ″ | —OCH₃ | $C_8H_9N_3O$ | 25.8 | 25.2 |
| 61. | ″ | —O—C₆H₅ | $C_{13}H_{11}N_3O$ | 18.7 | 19.1 |
| 62. | ″ | —SH | $C_7H_7N_3S$ | 25.5 | 25.7 |
| 63. | ″ | —SC₂H₅ | $C_9H_{11}N_3S$ | 21.8 | 22.3 |
| 64. | —NH₂ | —SO₂—CH₃ | $C_8H_9N_3O_2S$ | 19.9 | 20.5 |
| 65. | ″ | —NH—CH₃ | $C_8H_{10}N_4$ | 34.6 | 34.2 |
| 66. | ″ | —NH—C₂H₅ | $C_9H_{12}N_4$ | 31.8 | 31.5 |
| 67. | ″ | —NHCH₂CH₂CH₂OCH₃ | $C_{11}H_{16}N_4O$ | 25.5 | 25.2 |
| 68. | ″ | —NH—C₆H₅ | $C_{13}H_{12}N_4$ | 25.0 | 25.5 |
| 69. | ″ | —NH—CH₂—C₆H₅ | $C_{14}H_{14}N_4$ | 23.6 | 24.1 |
| 70. | ″ | (indol-3-yl)CH₂—NH— | $C_{16}H_{14}N_5$ | 25.4 | 25.0 |
| 71. | ″ | —N(CH₃)₂ | $C_9H_{12}N_4$ | 31.8 | 31.6 |
| 72. | ″ | —N(CH₃)(CH₂CH₂OH) | $C_{10}H_{14}ON_4$ | 27.2 | 27.7 |
| 73. | —NH₂ | —N(CH₂CH₂OH)₂ | $C_{11}H_{16}O_2N_4$ | 23.7 | 24.2 |
| 74. | ″ | morpholino | $C_{11}H_{14}ON_4$ | 25.7 | 26.2 |
| 75. | ″ | piperidino | $C_{12}H_{16}N_4$ | 25.9 | 26.3 |
| 76. | ″ | —NH—N(CH₃)₂ | $C_9H_{13}N_5$ | 36.6 | 36.1 |
| 77. | ″ | —NHCH₂CH₂N(C₂H₅)₂ | $C_{13}H_{21}N_5$ | 28.3 | 28.1 |
| 78. | ″ | —NHCH₂CH₂N(CH₂)₂ | $C_{11}H_{15}N_5$ | 32.3 | 32.2 |
| 79. | ″ | —N(CH₃)(OCH₃) | $C_9H_{12}ON_4$ | 29.2 | 29.0 |
| 80. | ″ | —N(C₃H₇(iso))(O—C₂H₅) | $C_{12}H_{18}ON_4$ | 23.9 | 23.3 |
| 81. | —NH—CH₃ | —Cl | $C_8H_8N_3Cl$ | 23.2 | 23.5 |
| 82. | ″ | —CN | $C_9H_8N_4$ | 32.6 | 32.2 |
| 83. | ″ | —OH | $C_8H_9ON_3$ | 25.8 | 26.2 |
| 84. | ″ | —OC₂H₅ | $C_{10}H_{13}ON_3$ | 22.0 | 22.5 |
| 85. | —NH—CH₃ | —SO₂—C₂H₅ | $C_{10}H_{13}N_3O_2S$ | 17.6 | 17.5 |
| 86. | ″ | —NH—C₃H₇(n) | $C_{11}H_{16}N_4$ | 27.5 | 27.1 |
| 87. | ″ | —NH—C₅H₁₁(iso) | $C_{13}H_{20}N_4$ | 24.1 | 23.5 |
| 88. | ″ | —NH—cyclohexyl | $C_{14}H_{20}N_4$ | 23.0 | 22.5 |
| 89. | ″ | —NH—CH₂—C₆H₅ | $C_{15}H_{16}N_4$ | 22.2 | 22.0 |
| 90. | ″ | —NH—naphthyl | $C_{18}H_{16}N_4$ | 19.4 | 19.0 |

-continued

| No. | $Z_1$ | $Z_2$ | Empirical Formula | Cal'd. N% | Found N% |
|---|---|---|---|---|---|
| 91. | $-NH-CH_3$ | furfurylamino group (HC=CH-O-CH-CH$_2$-NH–) | $C_{13}H_{15}N_4O$ | 23.0 | 22.5 |
| 92. | " | $-N(C_2H_5)_2$ | $C_{12}H_{18}N_4$ | 25.7 | 26.1 |
| 93. | " | $-N(CH_2CH_2CN)(CH_2CH_2OH)$ | $C_{13}H_{17}N_5O$ | 27.0 | 26.5 |
| 94. | " | pyrrolidino | $C_{12}H_{16}N_4$ | 25.9 | 26.4 |
| 95. | " | 4-methylpiperazino | $C_{13}H_{19}N_5$ | 28.6 | 28.2 |
| 96. | " | $-NH-N(C_2H_5)_2$ | $C_{12}H_{19}N_5$ | 30.0 | 30.6 |
| 97. | $-NH-CH_3$ | $-NHCH_2CH_2-N(CH_3)_2$ | $C_{12}H_{19}N_5$ | 30.0 | 30.3 |
| 98. | " | $-N(CH_2CH_2OH)(O-C_2H_5)$ | $C_{12}H_{18}N_4O_2$ | 22.4 | 22.0 |
| 99. | $-NH-C_2H_5$ | $-Cl$ | $C_9H_{10}ClN_3$ | 21.5 | 21.3 |
| 100. | " | $-CN$ | $C_{10}H_{10}N_4$ | 30.1 | 30.5 |
| 101. | " | $-OH$ | $C_9H_{11}N_3O$ | 23.7 | 23.2 |
| 102. | " | $-OC_3H_7(n)$ | $C_{12}H_{17}N_3O$ | 19.2 | 19.0 |
| 103. | " | $-SCH_3$ | $C_{10}H_{13}N_3S$ | 20.3 | 20.7 |
| 104. | " | $-SO_2-C_3H_7(n)$ | $C_{12}H_{17}N_3O_2S$ | 15.7 | 15.5 |
| 105. | " | $-NH-CH_3$ | $C_{10}H_{14}N_4$ | 29.5 | 29.0 |
| 106. | " | $-NH-CH_2-CH_2-OCH_3$ | $C_{12}H_{18}N_4O$ | 23.9 | 23.3 |
| 107. | " | $-NH-C_6H_{13}(n)$ | $C_{15}H_{24}N_4$ | 21.5 | 21.0 |
| 108. | $-NH-C_2H_5$ | $-N(CH_3)_2$ | $C_{11}H_{18}N_4$ | 27.5 | 27.3 |
| 109. | $-NH-C_2H_5$ | piperidino | $C_{14}H_{20}N_4$ | 23.0 | 22.5 |
| 110. | " | $-NH-N(CH_3)_2$ | $C_{11}H_{17}N_5$ | 32.0 | 31.6 |
| 111. | " | $-NHCH_2CH_2N(C_2H_5)_2$ | $C_{15}H_{25}N_5$ | 25.5 | 26.0 |
| 112. | " | $-N(CH_2C_6H_5)(O-CH_2C_6H_5)$ | $C_{23}H_{24}N_4O$ | 15.1 | 15.5 |
| 113. | $-NH-C_3H_7(n)$ | $-OH$ | $C_{10}H_{13}N_3O$ | 22.0 | 22.4 |
| 114. | " | $-C-C_3H_7(iso)$ | $C_{13}H_{19}N_3O$ | 18.0 | 18.5 |
| 115. | " | $-SO_2-C_5H_{11}(iso)$ | $C_{15}H_{23}N_3O_2S$ | 13.6 | 13.3 |
| 116. | $-NH-C_3H_7(n)$ | $-NH-CH_3$ | $C_{11}H_{18}N_4$ | 27.5 | 28.0 |
| 117. | " | $-NH-C_3H_7(iso)$ | $C_{13}H_{20}N_4$ | 24.1 | 24.5 |
| 118. | " | $-NH-$cyclohexyl | $C_{16}H_{24}N_4$ | 20.6 | 21.0 |
| 119. | " | $-NH-C_6H_5$ | $C_{16}H_{18}N_4$ | 21.1 | 21.5 |
| 120. | $-NH-C_3H_7(n)$ | $-N(CH_3)_2$ | $C_{12}H_{18}N_4$ | 25.7 | 26.0 |
| 121. | " | $-N(CH_2C_6H_5)(CH_2-CH_2-OH)$ | $C_{19}H_{24}N_4O$ | 17.3 | 17.5 |

-continued

| No. | $Z_1$ | $Z_2$ | Empirical Formula | Cal'd. N% | Found N% |
|---|---|---|---|---|---|
| 122. | " | —NH—N(piperidine-like ring with O) | $C_{14}H_{21}N_5O$ | 25.5 | 26.1 |
| 123. | " | —NHCH$_2$CH$_2$N(CH$_3$)$_2$ | $C_{14}H_{23}N_5$ | 26.8 | 26.4 |
| 124. | —NH—C$_3$H$_7$(n) | —N(CH$_3$)(OCH$_3$) | $C_{12}H_{18}N_4O$ | 23.9 | 23.2 |
| 125. | —NH—C$_3$H$_7$(iso) | —NHCH$_2$CH$_2$CH$_2$OCH$_3$ | $C_{14}H_{22}N_4O$ | 21.4 | 21.0 |
| 126. | " | —N(C$_2$H$_5$)$_2$ | $C_{14}H_{22}N_4$ | 22.8 | 23.0 |
| 127. | —NH—C$_4$H$_9$(n) | —Cl | $C_{11}H_{14}ClN_3$ | 18.8 | 19.0 |
| 128. | " | —OH | $C_{11}H_{15}N_3O$ | 20.5 | 21.0 |
| 129. | " | —O—C$_4$H$_9$(n) | $C_{15}H_{23}N_3O$ | 16.1 | 16.4 |
| 130. | " | —NH—CH$_3$ | $C_{12}H_{18}N_4$ | 25.7 | 25.0 |
| 131. | " | —NHCH$_2$CH$_2$OH | $C_{13}H_{20}N_4O$ | 22.6 | 23.0 |
| 132. | —NH—C$_4$H$_9$(iso) | —N(CH$_3$)$_2$ | $C_{13}H_{20}N_4$ | 24.1 | 23.8 |
| 133. | —NH—C$_4$H$_9$(iso) | —N(piperazine)—CH$_3$ | $C_{16}H_{25}N_5$ | 24.4 | 24.1 |
| 134. | —NH—C$_4$H$_9$(sek) | —N(C$_2$H$_5$)$_2$ | $C_{15}H_{24}N_4$ | 21.5 | 22.0 |
| 135. | " | —NH—N(CH$_3$)$_2$ | $C_{13}H_{21}N_5$ | 28.3 | 28.5 |
| 136. | " | —N(CH$_2$CH$_2$OH)(O—CH$_2$CH$_2$CH$_3$) | $C_{16}H_{26}N_4O_2$ | 18.3 | 18.7 |
| 137. | —NH—C$_4$H$_9$(tert) | —NH—C$_2$H$_5$ | $C_{13}H_{20}N_4$ | 24.1 | 24.5 |
| 138. | " | —NH—CH$_2$—CH$_2$—CN | $C_{14}H_{19}N_5$ | 27.2 | 27.5 |
| 139. | —NH—C$_5$H$_{11}$(n) | —NH—CH$_3$ | $C_{13}H_{20}N_4$ | 24.1 | 24.5 |
| 140. | " | —N(CH$_3$)$_2$ | $C_{14}H_{22}N_4$ | 22.8 | 23.0 |
| 141. | —NH—C$_5$H$_{11}$(n) | —NH—CH$_2$-(2-pyridyl) | $C_{18}H_{23}N_5$ | 22.7 | 23.2 |
| 142. | —NH—C$_5$H$_{11}$(iso) | —NH—N(CH$_3$)$_2$ | $C_{14}H_{23}N_5$ | 26.8 | 27.2 |
| 143. | —NH—C$_6$H$_{13}$(n) | —N(C$_2$H$_5$)$_2$ | $C_{17}H_{28}N_4$ | 19.4 | 19.0 |
| 144. | —NH—C$_6$H$_{13}$(n) | —N(morpholine) | $C_{12}H_{26}N_4O$ | 18.5 | 18.9 |
| 145. | " | —NHCH$_2$CH$_2$N(CH$_3$)$_2$ | $C_{17}H_{29}N_5$ | 23.1 | 23.3 |
| 146. | —NHCH$_2$CH$_2$OH | —NH—CH$_3$ | $C_{10}H_{14}N_4O$ | 27.2 | 27.5 |
| 147. | " | —NHCH$_2$CH$_2$OCH$_3$ | $C_{13}H_{20}N_4O_2$ | 21.2 | 21.5 |
| 148. | " | —N(CH$_3$)$_2$ | $C_{11}H_{16}N_4O$ | 25.5 | 26.0 |
| 149. | " | —N(morpholine) | $C_{13}H_{18}N_4O_2$ | 21.4 | 21.7 |
| 150. | —NHCH$_2$CH$_2$OH | —N(piperidine) | $C_{14}H_{20}N_4O$ | 21.5 | 21.8 |
| 151. | " | —NHCH$_2$CH$_2$N(CH$_2$)(CH$_2$) | $C_{13}H_{19}N_5O$ | 26.8 | 27.2 |
| 152. | —NHCH$_2$CH$_2$OCH$_3$ | —NH—CH$_3$ | $C_{11}H_{16}N_4O$ | 25.5 | 25.8 |
| 153. | " | —N(CH$_3$)$_2$ | $C_{12}H_{18}N_4O$ | 23.9 | 24.3 |
| 154. | —NHCH$_2$CH$_2$O—C$_6$H$_5$ | —N(C$_2$H$_5$)$_2$ | $C_{19}H_{24}N_4O$ | 17.3 | 17.5 |
| 155. | —NHCH$_2$CH$_2$CH$_2$CN | —NH—C$_2$H$_5$ | $C_{13}H_{17}N_5$ | 28.8 | 28.2 |
| 156. | —NHCH$_2$CH$_2$CH$_2$CN | —N(CH$_3$)(CH$_2$CH$_2$OH) | $C_{14}H_{19}N_5O$ | 25.6 | 26.0 |
| 157. | " | —N(C$_2$H$_5$)$_2$ | $C_{15}H_{21}N_5$ | 25.8 | 26.3 |

-continued

| No. | Z₁ | Z₂ | Empirical Formula | Cal'd. N% | Found N% |
|---|---|---|---|---|---|
| 158. | " | −NH−N(CH₃)(C₆H₅) | $C_{18}H_{20}N_6$ | 26.2 | 27.0 |
| 159. | −NH−(2-naphthyl) | −NH−(2-naphthyl) | $C_{27}H_{20}N_4$ | 14.0 | 13.5 |
| 160. | −NH−C₂H₅ | −NH−cyclohexyl | $C_{15}H_{22}N_4$ | 21.7 | 22.2 |
| 161. | " | −NH−CH₂−CH₂−C₆H₅ | $C_{17}H_{20}N_4$ | 20.0 | 20.4 |
| 162. | " | −NH−C₆H₄−CH₃ | $C_{16}H_{18}N_4$ | 21.1 | 21.5 |
| 163. | −NH−C₄H₉(n) | −NH−C₆H₄−OCH₃ | $C_{18}H_{22}N_4O$ | 18.1 | 18.6 |
| 164. | −NH−cyclohexyl | −NH−C₆H₄−CN | $C_{20}H_{21}N_5$ | 21.1 | 21.7 |
| 165. | " | −NH₂ | $C_{13}H_{18}N_4$ | 24.3 | 24.5 |
| 166. | " | −NH−CH₃ | $C_{14}H_{20}N_4$ | 23.0 | 23.5 |
| 167. | −NH−cyclohexyl | −NH−CH₂−CH=CH₂ | $C_{16}H_{22}N_4$ | 20.7 | 21.0 |
| 168. | " | −NHCH₂CH₂CH₂OCH₃ | $C_{17}H_{26}N_4O$ | 19.2 | 19.5 |
| 169. | " | −N(CH₃)₂ | $C_{15}H_{22}N_4$ | 21.7 | 22.2 |
| 170. | " | −NH−N(piperazine)N−CH₃ | $C_{18}H_{28}N_6$ | 25.6 | 26.0 |
| 171. | " | −NHCH₂CH₂CH₂N(CH₃)₂ | $C_{19}H_{29}N_5$ | 22.2 | 22.5 |
| 172. | −NH−cyclohexyl | −N(morpholino) | $C_{17}H_{24}N_4O$ | 18.7 | 19.1 |
| 173. | −NH−CH₂−C₆H₅ | −NH₂ | $C_{14}H_{14}N_4$ | 23.5 | 24.0 |
| 174. | " | −NH−C₂H₅ | $C_{16}H_{18}N_4$ | 21.2 | 22.0 |
| 175. | " | −N(C₂H₅)₂ | $C_{18}H_{22}N_4$ | 19.0 | 19.3 |
| 176. | " | −NHCH₂CH₂OCH₃ | $C_{17}H_{20}N_4O$ | 18.9 | 18.4 |
| 177. | " | −NHCH₂CH₂N(C₂H₅)₂ | $C_{20}H_{27}N_5$ | 20.8 | 21.4 |
| 178. | −NH−CH₂−C₆H₅ | −NH−CH₂−CH₂−(2-pyridyl) | $C_{21}H_{21}N_5$ | 20.4 | 20.6 |
| 179. | −NH−CH₂−C₆H₅ | −N(CH₂C₆H₅)(OCH₃) | $C_{22}H_{22}N_4O$ | 15.6 | 16.0 |

-continued

| No. | Z₁ | Z₂ | Empirical Formula | Cal'd. N% | Found N% |
|---|---|---|---|---|---|
| 180. | −NH−CH₂−CH₂−C₆H₅ | −NH−CH₃ | $C_{18}H_{18}N_4$ | 21.1 | 21.5 |
| 181. | " | −N(CH₃)₂ | $C_{17}H_{20}N_4$ | 20.0 | 20.5 |
| 182. | " | −N(morpholino) | $C_{17}H_{23}N_4O$ | 18.7 | 19.0 |
| 183. | −NH−C₆H₅ | −NH₂ | $C_{13}H_{12}N_4$ | 25.0 | 24.7 |
| 184. | " | −NH−CH₃ | $C_{14}H_{14}N_4$ | 23.6 | 24.2 |
| 185. | " | −NH−C₃H₇(n) | $C_{16}H_{18}N_4$ | 21.1 | 21.3 |
| 186. | " | −NHCH₂CH₂OH | $C_{15}H_{16}N_4O$ | 20.9 | 21.5 |
| 187. | −NH−C₆H₅ | −N(CH₃)₂ | $C_{15}H_{16}N_4$ | 22.2 | 22.0 |
| 188. | " | −N(CH₂CH₂CN)₂ | $C_{19}H_{18}N_6$ | 25.5 | 25.9 |
| 189. | −NH−C₆H₅ | −N(morpholino) | $C_{17}H_{18}N_4O$ | 19.1 | 19.7 |
| 190. | " | −NH−N(C₂H₅)₂ | $C_{17}H_{21}N_5$ | 23.7 | 24.3 |
| 191. | " | −NHCH₂CH₂CH₂N(CH₃)₂ | $C_{18}H_{23}N_5$ | 22.7 | 22.3 |
| 192. | " | −N(CH₃)(O−CH₃) | $C_{15}H_{16}N_4O$ | 20.9 | 21.4 |
| 193. | −NH−C₆H₄−Cl | −NH−CH₃ | $C_{14}H_{13}ClN_4$ | 20.6 | 20.2 |
| 194. | −NH−C₆H₄−CH₃ | −NH−CH₃ | $C_{15}H_{16}N_4$ | 22.2 | 22.8 |
| 195. | −NH−C₆H₃(CH₃)₂ | −N(CH₃)₂ | $C_{17}H_{20}N_4$ | 20.0 | 20.5 |
| 196. | −NH−C₆H₄−OCH₃ | " | $C_{16}H_{18}N_4O$ | 19.9 | 20.3 |
| 197. | −NH−CH₂−(furyl) | −NH−CH₃ | $C_{12}H_{14}N_4O$ | 23.1 | 23.5 |
| 198. | " | −N(CH₃)₂ | $C_{14}H_{16}N_4O$ | 21.9 | 21.5 |
| 199. | " | −NHCH₂CH₂CH₂N(C₂H₅)₂ | $C_{19}H_{27}N_5O$ | 20.5 | 20.9 |
| 200. | −NH−CH₂−(2-pyridyl) | −NH−CH₃ | $C_{14}H_{15}N_5$ | 27.7 | 27.2 |
| 201. | −NH−CH₂−(4-pyridyl) | −NH−CH₃ | $C_{14}H_{15}N_5$ | 27.7 | 28.2 |

-continued

| No. | $Z_1$ | $Z_2$ | Empirical Formula | Cal'd. N% | Found N% |
|---|---|---|---|---|---|
| 202. | $-NH-CH_2-CH_2-$(2-pyridyl) | $-NH-CH_3$ | $C_{15}H_{17}N_5$ | 26.2 | 26.0 |
| 203. | $-NH-CH_2-CH_2-$(4-pyridyl) | $-NH-CH_3$ | $C_{15}H_{17}N_5$ | 26.2 | 26.6 |
| 204. | $-NH-HC-CH_2-CH_2-CH_2-S(O_2)$ (tetrahydrothiophene-1,1-dioxide-3-yl) | $-NH-CH_3$ | $C_{12}H_{16}N_4O_2S$ | 20.0 | 20.5 |
| 205. | " | $-N(CH_3)_2$ | $C_{13}H_{18}N_4O_2S$ | 19.0 | 18.7 |
| 206. | " | $-N$(morpholino) | $C_{15}H_{20}N_4O_3S$ | 16.7 | 17.1 |
| 207. | " | $-NH-N(CH_3)_2$ | $C_{13}H_{19}N_5O_2S$ | 22.7 | 22.2 |
| 208. | (indol-3-yl)$-CH_2-NH-$ | $-NH-CH_3$ | $C_{17}H_{17}N_5$ | 24.1 | 24.5 |
| 209. | " | $-N(CH_3)_2$ | $C_{18}H_{19}N_5$ | 23.0 | 23.5 |
| 210. | " | $-N$(morpholino) | $C_{20}H_{21}N_5O$ | 20.2 | 20.5 |
| 211. | $NH-$(cyclohexyl) | $-Cl$ | $C_{13}H_{16}ClN_3$ | 16.9 | 16.5 |
| 212. | " | $-OH$ | $C_{13}H_{17}N_3O$ | 18.2 | 18.6 |
| 213. | " | $-OCH_3$ | $C_{14}H_{19}N_3O$ | 17.1 | 17.6 |
| 214. | " | $-CN$ | $C_{14}H_{16}N_4$ | 25.0 | 25.3 |
| 215. | " | $-SO_2-CH_2-$phenyl | $C_{20}H_{23}N_3O_2S$ | 11.4 | 11.2 |
| 216. | $-NH-CH_2-$phenyl | $-Cl$ | $C_{14}H_{12}ClN_3$ | 16.3 | 16.0 |
| 217. | " | $-OH$ | $C_{14}H_{13}N_3O$ | 17.6 | 18.0 |
| 218. | " | $-O-CH_3$ | $C_{15}H_{15}N_3O$ | 16.6 | 16.0 |
| 219. | " | $-S-C_4H_9(n)$ | $C_{18}H_{21}N_3S$ | 21.5 | 21.8 |
| 220. | $-NH-$phenyl | $-Cl$ | $C_{13}H_{10}ClN_3$ | 17.3 | 17.0 |
| 221. | $-NH-$phenyl | $-CN$ | $C_{14}H_{10}N_4$ | 23.9 | 24.3 |
| 222. | " | $-OH$ | $C_{13}H_{11}N_3O$ | 18.7 | 18.5 |
| 223. | " | $-OCH_3$ | $C_{14}H_{13}N_3O$ | 17.6 | 17.3 |
| 224. | " | $-SCH_3$ | $C_{14}H_{13}N_3S$ | 16.5 | 16.0 |
| 225. | $-N(CH_3)_2$ | $-Cl$ | $C_9H_{10}ClN_3$ | 21.5 | 21.0 |
| 226. | " | $-CN$ | $C_{10}H_{10}N_4$ | 30.1 | 30.5 |
| 227. | " | $-OH$ | $C_9H_{11}N_3O$ | 23.7 | 23.4 |
| 228. | " | $-OCH_3$ | $C_{10}H_{13}N_3O$ | 22.0 | 22.3 |
| 229. | " | $-SO_2-C_2H_5$ | $C_{11}H_{15}N_3O_2S$ | 16.6 | 17.0 |
| 230. | " | $-NH-CH_3$ | $C_{10}H_{14}N_4$ | 29.5 | 29.1 |
| 231. | " | $-NH-C_3H_7(n)$ | $C_{12}H_{18}N_4$ | 25.7 | 26.2 |
| 232. | " | $-NH-C_6H_{13}(n)$ | $C_{15}H_{24}N_4$ | 21.5 | 21.8 |
| 233. | $-N(CH_3)_2$ | $-NH-$cyclohexyl | $C_{15}H_{22}N_4$ | 21.7 | 21.5 |

-continued

| No. | $Z_1$ | $Z_2$ | Empirical Formula | Cal'd N% | Found N% |
|---|---|---|---|---|---|
| 234. | " | $-NH-CH_2-$(phenyl) | $C_{16}H_{18}N_4$ | 21.1 | 20.7 |
| 235. | " | $-NH-$(phenyl) | $C_{15}H_{16}N_4$ | 22.2 | 22.6 |
| 236. | " | $-NH-$(naphthyl) | $C_{19}H_{18}N_4$ | 18.5 | 18.9 |
| 237. | " | (furfurylamino) $-CH_2-NH-$ | $C_{14}H_{16}N_4O$ | 21.9 | 21.5 |
| 238. | " | $-N(C_2H_5)_2$ | $C_{13}H_{20}N_4$ | 24.1 | 23.8 |
| 239. | $-N(CH_3)_2$ | $-N(CH_2CH_2CN)(CH_2CH_2OH)$ | $C_{14}H_{19}N_5O$ | 25.6 | 26.0 |
| 240. | " | $-N$(pyrrolidine) | $C_{13}H_{18}N_4$ | 24.3 | 24.5 |
| 241. | $-N(CH_3)_2$ | $-N$(N-methylpiperazine)$-CH_3$ | $C_{14}H_{21}N_5$ | 27.0 | 27.4 |
| 242. | " | $-NH-N(C_2H_5)_2$ | $C_{13}H_{21}N_5$ | 28.3 | 27.9 |
| 243. | " | $-NHCH_2CH_2N(CH_3)_2$ | $C_{14}H_{23}N_5$ | 26.8 | 26.6 |
| 244. | " | $-N(CH_2CH_2OH)(O-C_2H_5)$ | $C_{13}H_{20}N_4O_2$ | 21.2 | 21.6 |
| 245. | $-N(C_2H_5)_2$ | $-Cl$ | $C_{11}H_{14}ClN_3$ | 18.8 | 18.5 |
| 246. | " | $-CN$ | $C_{12}H_{14}N_4$ | 26.2 | 26.6 |
| 247. | " | $-OH$ | $C_{11}H_{15}N_3O$ | 20.5 | 21.0 |
| 248. | " | $-OCH_3$ | $C_{12}H_{17}N_3O$ | 19.2 | 19.0 |
| 249. | " | $-SC_2H_5$ | $C_{13}H_{19}N_3S$ | 16.8 | 17.2 |
| 250. | $-N(C_2H_5)_2$ | $-SO_2-C_4H_9(n)$ | $C_{15}H_{23}N_3SO_2$ | 13.6 | 13.5 |
| 251. | $-N(C_2H_5)_2$ | $-NH-CH_3$ | $C_{12}H_{17}N_4$ | 25.7 | 25.5 |
| 252. | " | $-NHCH_2CH_2OCH_3$ | $C_{15}H_{24}N_4O$ | 20.3 | 20.0 |
| 253. | " | $-NH-$(cyclohexyl) | $C_{17}H_{25}N_4$ | 19.6 | 19.5 |
| 254. | " | $-NH-CH_2-$(phenyl) | $C_{18}H_{22}N_4$ | 19.0 | 19.4 |
| 255. | " | $-NH-$(phenyl) | $C_{17}H_{20}N_4$ | 20.0 | 20.2 |
| 256. | " | $-N$(piperidine) | $C_{16}H_{24}N_4$ | 20.6 | 21.0 |
| 257. | " | $-NH-N(CH_3)_2$ | $C_{13}H_{21}N_5$ | 28.3 | 28.0 |
| 258. | " | $-NHCH_2CH_2OH_2N(CH_3)_2$ | $C_{16}H_{27}N_5$ | 24.2 | 24.5 |
| 259. | $-N(C_2H_5)_2$ | $-N(CH_3)(OCH_3)$ | $C_{13}H_{20}N_4O$ | 22.6 | 22.2 |
| 260. | $-N(CH_2CH_2CN)(CH_2CH_2OH)$ | $-OCH_3$ | $C_{13}H_{16}N_4O_2$ | 21.5 | 21.3 |

-continued

| No. | $Z_1$ | $Z_2$ | Empirical Formula | Cal'd. N% | Found N% |
|---|---|---|---|---|---|
| 261. | '' | −N(CH₂CH₂)₂O (morpholino) | $C_{16}H_{21}N_5O_2$ | 22.2 | 22.6 |
| 262. | −N(CH₂CH₂OH)₂ | −NH₂ | $C_{11}H_{16}N_4O_2$ | 23.7 | 23.4 |
| 263. | −N(CH₂CH₂OH)₂ | −N(CH₃)₂ | $C_{13}H_{20}N_4O_2$ | 21.2 | 21.5 |
| 264. | '' | −NH−C₆H₅ | $C_{17}H_{20}N_4O_2$ | 17.9 | 18.2 |
| 265. | −N(CH₂CH₂CN)₂ | −OCH₃ | $C_{14}H_{15}N_5O$ | 26.0 | 26.3 |
| 266. | '' | −N(CH₃)₂ | $C_{15}H_{18}N_6$ | 29.8 | 29.5 |
| 267. | −N(CH₃)(CH₂CH₂OH) | −NH₂ | $C_{10}H_{14}N_4O$ | 27.2 | 27.5 |
| 268. | '' | −NH−CH₃ | $C_{11}H_{16}N_4O$ | 25.5 | 25.8 |
| 269. | '' | −NH−CH₂−(2-pyridyl) | $C_{16}H_{24}N_5O$ | 23.2 | 23.7 |
| 270. | '' | −NH−C₆H₅ | $C_{16}H_{18}N_4O$ | 19.9 | 19.5 |
| 271. | '' | −NH−N(CH₃)₂ | $C_{12}H_{19}N_5O$ | 28.1 | 27.8 |
| 272. | −N(C₃H₇(iso))(CH₂CH₂OH) | −NHCH₂CH₂CH₂OCH₃ | $C_{16}H_{26}N_4O_2$ | 13.8 | 14.2 |
| 273. | −N(C₄H₉(n))(CH₂CH₂OH) | −NH−CH₃ | $C_{14}H_{22}N_4O$ | 21.4 | 21.0 |
| 274. | −N(C₄H₉(n))(CH₂CH₂OH) | −N(CH₂CH₂)₂O (morpholino) | $C_{17}H_{26}N_4O_2$ | 17.6 | 18.0 |
| 275. | −N(C₄H₉(n))(CH₂CH₂OH) | −NHCH₂CH₂N(CH₃)₂ | $C_{17}H_{29}N_5O$ | 21.9 | 21.7 |
| 276. | −N(cyclohexyl)(CH₂CH₂OH) | −NH−CH₃ | $C_{16}H_{23}N_4O$ | 19.4 | 19.0 |
| 277. | −N(cyclohexyl)(CH₂CH₂OH) | −NH−cyclohexyl | $C_{21}H_{32}N_4O$ | 15.7 | 16.3 |
| 278. | −N(CH₂C₆H₅)(CH₂CH₂OH) | −NH₂ | $C_{16}H_{18}N_4O$ | 19.9 | 19.5 |
| 279. | −N(CH₂C₆H₅)(CH₂CH₂OH) | −NH−CH₃ | $C_{17}H_{20}N_4O$ | 18.9 | 19.5 |

-continued

| No. | $Z_1$ | $Z_2$ | Empirical Formula | Cal'd. N% | Found N% |
|---|---|---|---|---|---|
| 280. | " | -NHCH$_2$CH$_2$-(pyridyl) | C$_{23}$H$_{25}$N$_5$O | 18.1 | 18.5 |
| 281. | -N(C$_3$H$_7$(n))$_2$ | -Cl | C$_{13}$H$_{18}$ClN$_3$ | 16.7 | 16.5 |
| 282. | " | -NH$_2$ | C$_{13}$H$_{20}$N$_4$ | 24.1 | 24.5 |
| 283. | " | -CN | C$_{14}$H$_{18}$N$_4$ | 23.1 | 23.7 |
| 284. | -N(C$_3$H$_7$(n))$_2$ | -OH | C$_{13}$H$_{19}$N$_3$O | 18.0 | 18.4 |
| 285. | " | -OCH$_3$ | C$_{14}$H$_{21}$N$_3$O | 17.0 | 17.5 |
| 286. | " | -SO$_2$-CH$_3$ | C$_{14}$H$_{21}$N$_3$O$_2$S | 14.2 | 13.8 |
| 287. | " | -NH-CH$_3$ | C$_{14}$H$_{22}$N$_4$ | 22.8 | 23.2 |
| 288. | " | -NH-C$_3$H$_7$(n) | C$_{16}$H$_{26}$N$_4$ | 20.5 | 21.0 |
| 289. | " | -NH-(cyclohexyl) | C$_{19}$H$_{30}$N$_4$ | 17.8 | 17.5 |
| 290. | " | -NH-(phenyl) | C$_{19}$H$_{24}$N$_4$ | 18.2 | 18.5 |
| 291. | " | -N(CH$_3$)$_2$ | C$_{15}$H$_{24}$N$_4$ | 21.5 | 20.8 |
| 292. | " | -NH-N(morpholino) | C$_{17}$H$_{27}$N$_5$O | 22.1 | 22.5 |
| 293. | -N(C$_3$H$_7$(n))$_2$ | -NHCH$_2$CH$_2$N(CH$_3$)$_2$ | C$_{17}$H$_{29}$N$_5$ | 23.1 | 23.6 |
| 294. | " | -N(CH$_3$)(OCH$_3$) | C$_{15}$H$_{23}$N$_4$O | 20.3 | 20.0 |
| 295. | -N(C$_3$H$_7$(iso))$_2$ | -NH$_2$ | C$_{13}$H$_{20}$N$_4$ | 24.2 | 24.6 |
| 296. | " | -OH | C$_{13}$H$_{19}$N$_3$O | 18.0 | 18.5 |
| 297. | -N(C$_3$H$_7$(iso))$_2$ | -NH-CH$_3$ | C$_{14}$H$_{22}$N$_4$ | 22.8 | 22.5 |
| 298. | " | -N(piperidino) | C$_{18}$H$_{28}$N$_4$ | 18.7 | 19.1 |
| 299. | -N(C$_4$H$_9$(n))$_2$ | -Cl | C$_{15}$H$_{22}$ClN$_3$ | 15.0 | 15.4 |
| 300. | " | -CN | C$_{16}$H$_{22}$N$_4$ | 20.7 | 21.0 |
| 301. | -N(C$_4$H$_9$(n))$_2$ | -OH | C$_{15}$H$_{23}$N$_3$O | 16.1 | 16.5 |
| 302. | " | -OCH$_3$ | C$_{16}$H$_{25}$N$_3$O | 15.3 | 15.0 |
| 303. | " | -NH-CH$_3$ | C$_{16}$H$_{26}$N$_4$ | 20.4 | 20.8 |
| 304. | " | -NHCH$_2$CH$_2$OH | C$_{17}$H$_{28}$N$_4$O | 18.4 | 18.1 |
| 305. | " | -NH-(cyclohexyl) | C$_{21}$H$_{34}$N$_4$ | 16.4 | 16.8 |
| 306. | " | -N(morpholino) | C$_{19}$H$_{30}$N$_4$O | 17.0 | 17.3 |
| 307. | " | -NH-N(CH$_3$)$_2$ | C$_{17}$H$_{29}$N$_5$ | 23.1 | 23.5 |
| 308. | " | -NH-N(morpholino) | C$_{19}$H$_{31}$N$_5$O | 20.3 | 21.0 |
| 309. | -N(C$_4$H$_9$(iso))$_2$ | -NH$_2$ | C$_{15}$H$_{24}$N$_4$ | 21.5 | 21.9 |
| 310. | " | -NH-CH$_3$ | C$_{16}$H$_{26}$N$_4$ | 20.4 | 20.6 |
| 311. | -N(C$_4$H$_9$(iso))$_2$ | -NHCH$_2$CH$_2$OH | C$_{17}$H$_{28}$N$_4$O | 18.4 | 18.5 |
| 312. | -N(C$_4$H$_9$(iso))$_2$ | -NHCH$_2$CH$_2$N(CH$_3$)$_2$ | C$_{19}$H$_{33}$N$_5$ | 21.1 | 21.5 |
| 313. | -N(C$_5$H$_{11}$(n))$_2$ | -NH$_2$ | C$_{17}$H$_{28}$N$_4$ | 19.4 | 20.0 |

-continued

| No. | $Z_1$ | $Z_2$ | Empirical Formula | Cal'd. N% | Found N% |
|---|---|---|---|---|---|
| 314. | " | $-NH-CH_3$ | $C_{18}H_{30}N_4$ | 18.5 | 18.2 |
| 315. | " | $-NHCH_2CH_2OH$ | $C_{19}H_{32}N_4O$ | 16.9 | 17.5 |
| 316. | $-N(C_6H_{13}(n))_2$ | $-NH_2$ | $C_{19}H_{32}N_4$ | 17.7 | 18.0 |
| 317. | " | $-NH-CH_3$ | $C_{20}H_{34}N_4$ | 17.0 | 16.7 |
| 318. | " | $-NH-C_6H_5$ | $C_{25}H_{36}N_4$ | 14.3 | 14.7 |
| 319. | -N(morpholino) | $-NH_2$ | $C_{11}H_{14}N_4O$ | 25.7 | 26.2 |
| 320. | " | $-OH$ | $C_{11}H_{13}N_3O_2$ | 19.2 | 19.5 |
| 321. | " | $-NH-CH_3$ | $C_{12}H_{16}N_4O$ | 24.1 | 24.5 |
| 322. | -N(morpholino) | $-N(C_2H_5)_2$ | $C_{15}H_{22}N_4O$ | 20.4 | 21.0 |
| 323. | -N(pyrrolidino) | $-NH_2$ | $C_{11}H_{14}N_4$ | 27.7 | 28.0 |
| 324. | " | $-NH-CH_3$ | $C_{12}H_{16}N_4$ | 25.9 | 25.7 |
| 325. | " | $-N(CH_3)_2$ | $C_{13}H_{18}N_4$ | 24.3 | 25.0 |
| 326. | -N(piperidino) | $-OH$ | $C_{12}H_{15}N_3O$ | 19.3 | 19.5 |
| 327. | " | $-NH_2$ | $C_{12}H_{16}N_4$ | 25.9 | 25.5 |
| 328. | " | $-NH-CH_3$ | $C_{13}H_{18}N_4$ | 24.3 | 24.7 |
| 329. | " | $-NHCH_2CH_2OCH_3$ | $C_{16}H_{24}N_4O$ | 19.4 | 19.5 |
| 330. | " | $-N(CH_3)_2$ | $C_{14}H_{20}N_4$ | 22.9 | 23.0 |
| 331. | " | $-NH-C_6H_{11}$ | $C_{18}H_{26}N_4$ | 18.8 | 18.5 |
| 332. | -N(piperidino) | $-NH-C_6H_5$ | $C_{18}H_{20}N_4$ | 19.2 | 19.2 |
| 333. | -N(N-methylpiperazino) | $-NH_2$ | $C_{12}H_{17}N_5$ | 30.4 | 30.6 |
| 334. | " | $-NH-CH_3$ | $C_{13}H_{19}N_5$ | 28.5 | 28.7 |
| 335. | " | $-N(CH_3)_2$ | $C_{14}H_{21}N_5$ | 27.0 | 27.5 |
| 336. | -N(N-ethylpiperazino) | $-NH-CH_3$ | $C_{14}H_{21}N_5$ | 27.0 | 27.3 |
| 337. | $-N(CH_3)-N(CH_3)_2$ | $-NH-CH_3$ | $C_{11}H_{17}N_5$ | 32.0 | 32.3 |
| 338. | " | $-NHCH_2CH_2OH$ | $C_{12}H_{19}N_5O$ | 28.1 | 28.0 |
| 339. | $-NH-N(CH_3)_2$ | $-NH_2$ | $C_9H_{13}N_5$ | 36.7 | 37.0 |
| 340. | " | $-NH-CH_3$ | $C_{10}H_{15}N_5$ | 34.1 | 34.5 |
| 341. | $-NH-N(C_2H_5)_2$ | $-N(CH_3)_2$ | $C_{13}H_{21}N_5$ | 28.4 | 29.0 |
| 342. | " | $-N(CH_3)CH_2CH_2OH$ | $C_{14}H_{23}N_5O$ | 25.3 | 25.5 |
| 343. | " | $-NH-C_6H_5$ | $C_{17}H_{21}N_5$ | 23.8 | 24.0 |

-continued

| No. | $Z_1$ | $Z_2$ | Empirical Formula | Cal'd. N% | Found N% |
|---|---|---|---|---|---|
| 344. | -NH-N(CH₃)(C₆H₅) | -NH-CH₃ | $C_{15}H_{17}N_5$ | 26.2 | 26.6 |
| 345. | " | -N(CH₃)₂ | $C_{16}H_{19}N_5$ | 24.9 | 25.5 |
| 346. | -NH-N(pyrrolidine) | -NH-CH₃ | $C_{13}H_{17}N_5$ | 28.9 | 29.0 |
| 347. | " | -N(CH₃)₂ | $C_{14}H_{19}N_5$ | 27.3 | 27.5 |
| 348. | -NH-N(piperidine) | -NH₂ | $C_{12}H_{17}N_5$ | 30.3 | 31.6 |
| 349. | " | -NH-CH₃ | $C_{13}H_{19}N_5$ | 28.6 | 29.0 |
| 350. | " | -N(CH₃)₂ | $C_{14}H_{21}N_5$ | 27.1 | 26.8 |
| 351. | -NH-N(morpholine) | -NH-CH₃ | $C_{12}H_{17}N_5O$ | 28.4 | 28.6 |
| 352. | " | -N(CH₃)₂ | $C_{13}H_{19}N_5O$ | 26.8 | 27.0 |
| 353. | -NHCH₂CH₂N(CH₃)₂ | -NH-CH₃ | $C_{12}H_{19}N_5$ | 30.1 | 29.5 |
| 354. | -NHCH₂CH₂N(C₂H₅)₂ | -NHCH₂CH₂OH | $C_{15}H_{25}N_5O$ | 24.1 | 24.6 |
| 355. | -NHCH₂CH₂N(CH₃)₂ | -NH-CH₃ | $C_{13}H_{21}N_5$ | 28.4 | 29.0 |
| 356. | " | -NHCH₂CH₂OH | $C_{14}H_{23}N_5O$ | 25.3 | 25.5 |
| 357. | -NHCH₂CH₂N(C₂H₅)₂ | -NH-CH₃ | $C_{15}H_{25}N_5$ | 25.5 | 26.0 |
| 358. | -NHCH₂CH₂CH₂-N(morpholine) | -NH-CH₃ | $C_{13}H_{23}N_5O$ | 24.1 | 23.7 |
| 359. | -NHCH₂CH₂CH₂N(piperidine) | -NH-CH₃ | $C_{16}H_{25}N_5$ | 24.3 | 25.0 |
| 360. | -NHCH₂CH₂CH₂-N(pyrrolidine) | -NH-CH₃ | $C_{15}H_{23}N_5$ | 25.7 | 26.0 |
| 361. | -NHCH₂CH₂CH₂-N(N-methylpiperazine) | -NH-CH₃ | $C_{16}H_{26}N_6$ | 27.8 | 27.5 |
| 362. | -NH-OH | -NH-CH₃ | $C_8H_{10}N_4O$ | 31.5 | 31.9 |
| 363. | -N(CH₃)(OCH₃) | -NH-CH₃ | $C_{10}H_{14}N_4O$ | 27.2 | 27.7 |
| 364. | -N(CH₂CH₂OH)(OCH₃) | -NH-CH₃ | $C_{11}H_{16}N_4O$ | 25.5 | 25.1 |
| 365. | -N(CH₂C₆H₅)(OCH₃) | -NH-CH₃ | $C_{16}H_{18}N_4O$ | 19.8 | 19.2 |
| 366. | -N(CH(CH₃)₂)(OCH₂CH₃) | -NH-CH₃ | $C_{13}H_{20}N_4O$ | 22.6 | 23.0 |

-continued

| No. | $Z_1$ | $Z_2$ | Empirical Formula | Cal'd. N% | Found N% |
|---|---|---|---|---|---|
| 367. | -N(CH₂CH₂)₂O (azetidine-like with O) | —NH—CH₃ | $C_{11}H_{14}N_4O$ | 25.6 | 25.6 |
| 368. | -N(CH₂CH₂)₂O (morpholino) | —NH—CH₃ | $C_{12}H_{16}N_4O$ | 24.1 | 24.5 |
| 369. | —CN | —Cl | $C_8H_4ClN_3$ | 23.7 | 24.2 |
| 370. | —CN | —CN | $C_9H_4N_4$ | 33.3 | 33.8 |
| 371. | " | —OH | $C_8H_5N_3O$ | 26.4 | 27.0 |
| 372. | " | —OCH₃ | $C_9H_7N_3O$ | 24.3 | 24.0 |
| 373. | " | —NH₂ | $C_8H_6N_4$ | 35.4 | 35.8 |
| 374. | " | —NH—CH₃ | $C_9H_8N_4$ | 32.6 | 33.0 |
| 375. | " | —N(CH₃)₂ | $C_{10}H_{10}N_4$ | 30.1 | 30.5 |
| 376. | " | —N(CH₃)(CH₂CH₂OH) | $C_{11}H_{12}N_4O$ | 25.9 | 26.4 |
| 377. | —CN | —N(piperidine) | $C_{13}H_{14}N_4$ | 24.8 | 25.2 |
| 378. | " | —NH—N(CH₃)₂ | $C_{10}H_{11}N_5$ | 34.8 | 35.2 |
| 379. | " | —NH—OCH₃ | $C_9H_8N_4O$ | 29.8 | 29.5 |
| 380. | —OCH₃ | —Cl | $C_8H_7ClN_2O$ | 15.4 | 15.0 |
| 381. | —OC₂H₅ | —Cl | $C_9H_9ClN_2O$ | 14.3 | 14.7 |
| 382. | —OC₄H₉(n) | —Cl | $C_{11}H_{13}ClN_2O$ | 12.5 | 12.8 |
| 383. | —OCH₂CH₂OCH₃ | —Cl | $C_{10}H_{11}ClN_2O$ | 12.4 | 12.0 |
| 384. | —OCH₃ | —OCH₃ | $C_9H_{10}N_2O_2$ | 15.7 | 16.0 |
| 385. | " | —OC₂H₅ | $C_{10}H_{12}N_2O_2$ | 14.6 | 14.8 |
| 386. | —OC₂H₅ | —OC₂H₅ | $C_{11}H_{14}N_2O_2$ | 13.6 | 13.9 |
| 387. | —OCH₃ | —OCH₂CH₂OCH₃ | $C_{11}H_{14}N_2O_3$ | 12.6 | 12.2 |
| 388. | —OCH₂CH₂OCH₃ | —OCH₃ | $C_{11}H_{14}N_2O_3$ | 12.6 | 13.0 |
| 389. | —OCH₃ | —O—C₆H₅ | $C_{14}H_{12}N_2O_2$ | 11.7 | 11.9 |
| 390. | " | —SC₄H₉(n) | $C_{12}H_{16}N_2OS$ | 11.9 | 12.1 |
| 391. | —OC₂H₅ | —SC₂H₅ | $C_{11}H_{16}N_2OS$ | 12.6 | 13.0 |
| 392. | —OCH₃ | —S—C₆H₅ | $C_{14}H_{12}N_2OS$ | 10.9 | 12.1 |
| 393. | —OCH₃ | —O—CH₂—C₆H₅ | $C_{15}H_{14}N_2O_2$ | 11.0 | 11.5 |
| 394. | " | —NH—CH₃ | $C_9H_{11}N_3O$ | 23.7 | 23.5 |
| 395. | " | —NHCH₂CH₂OH | $C_{10}H_{13}N_3O_2$ | 20.8 | 21.2 |
| 396. | —OC₂H₅ | —NH—(CH₂)₃—OCH₃ | $C_{13}H_{19}N_3O_2$ | 16.9 | 17.3 |
| 397. | —OCH₂CH₂OCH₃ | —NH—C₆H₅ | $C_{16}H_{17}N_3O_2$ | 14.8 | 15.0 |
| 398. | —OC₄H₉(n) | —NH—(CH₂)₃—N(CH₃)₂ | $C_{16}H_{26}N_4O$ | 19.3 | 19.5 |
| 399. | —OCH₃ | —N(CH₃)(CH₂CH₂OH) | $C_{11}H_{15}N_3O_2$ | 19.0 | 19.3 |
| 400. | —OC₂H₅ | —N(morpholino) | $C_{13}H_{16}N_3O_2$ | 17.1 | 17.5 |
| 401. | —SCH₃ | —Cl | $C_8H_7ClN_2S$ | 14.1 | 14.5 |
| 402. | —SC₂H₅ | —Cl | $C_9H_9ClN_2S$ | 13.2 | 13.0 |
| 403. | —SC₄H₉(n) | —Cl | $C_{11}H_{13}ClN_2S$ | 11.7 | 12.1 |
| 404. | —SC₄H₉(n) | —OCH₃ | $C_{12}H_{16}N_2OS$ | 11.9 | 12.3 |
| 405. | —SC₂H₅ | —O—C₆H₅ | $C_{15}H_{14}N_2OS$ | 10.4 | 11.0 |
| 406. | —SC₄H₉(n) | —SC₄H₉(n) | $C_{15}H_{22}N_2S_2$ | 9.5 | 10.0 |
| 407. | —SCH₃ | —NH—CH₃ | $C_9H_{11}N_3S$ | 21.7 | 22.0 |
| 408. | —SC₂H₅ | —NH—(CH₂)₃—OCH₃ | $C_{13}H_{19}N_3OS$ | 15.8 | 16.0 |
| 409. | —SC₄H₉(n) | —NHCH₂CH₂OH | $C_{13}H_{19}N_3OS$ | 15.8 | 16.2 |
| 410. | " | —NH—C₆H₅ | $C_{17}H_{19}N_3S$ | 14.1 | 14.5 |
| 411. | " | —NH—(CH₂)₃—N(CH₃)₂ | $C_{16}H_{26}N_4S$ | 18.3 | 18.5 |

-continued

| No. | $Z_1$ | $Z_2$ | Empirical Formula | Cal'd. N% | Found N% |
|---|---|---|---|---|---|
| 412. | " | $-N(CH_3)CH_2CH_2OH$ | $C_{14}H_{21}N_3OS$ | 15.0 | 15.5 |
| 413. | " | –N(morpholino) | $C_{15}H_{21}N_3OS$ | 14.4 | 15.0 |
| 414. | $-SO_2-CH_3$ | $-Cl$ | $C_{10}H_{10}ClN_3O_2S$ | 15.5 | 15.0 |
| 415. | $-SO_2-C_4H_9(n)$ | $-Cl$ | $C_{13}H_{16}ClN_3O_2S$ | 13.4 | 13.8 |
| 416. | $-SO_2-C_6H_5$ | $-Cl$ | $C_{15}H_{12}ClN_3O_2S$ | 12.6 | 12.5 |
| 417. | $-SO_2-CH_3$ | $-CN$ | $C_{11}H_{10}N_4O_2S$ | 21.4 | 21.0 |
| 418. | " | $-OH$ | $C_{10}H_{11}N_3O_3S$ | 16.6 | 17.2 |
| 419. | " | $-OCH_3$ | $C_{11}H_{13}N_3O_3S$ | 15.7 | 15.3 |
| 420. | " | $-SCH_3$ | $C_{11}H_{13}N_3O_2S_2$ | 14.8 | 15.4 |
| 421. | " | $-SO_2-CH_3$ | $C_{11}H_{13}N_3O_4S_2$ | 13.3 | 12.9 |
| 422. | " | $-NH_2$ | $C_{10}H_{12}N_4O_2S$ | 22.2 | 22.6 |
| 423. | $-SO_2-C_2H_5$ | $-N(CH_3)_2$ | $C_{13}H_{18}N_4O_2S$ | 19.1 | 18.5 |
| 424. | " | $-NHCH_2CH_2OH$ | $C_{13}H_{18}N_4O_3S$ | 18.1 | 18.7 |
| 425. | $-SO_2-CH_3$ | $-N(CH_3)CH_2CH_2OH$ | $C_{13}H_{18}N_4O_3S$ | 18.1 | 18.3 |
| 426. | $-SO_2-CH_3$ | –N(morpholino) | $C_{14}H_{18}N_4O_3S$ | 17.4 | 17.6 |
| 427. | $-SO_2-C_2H_5$ | $-NH-(CH_2)_2-N(CH_3)_2$ | $C_{15}H_{23}N_5O_2S$ | 20.8 | 20.1 |
| 428. | $-SO_2-C_4H_9(n)$ | $-NHCH_2CH_2OH$ | $C_{15}H_{22}N_4O_2S$ | 17.4 | 17.8 |
| 429. | $-SO_2-CH_2-C_6H_5$ | $-NH-CH_3$ | $C_{17}H_{18}N_4O_2S$ | 16.4 | 16.0 |
| 430. | $-SO_2-C_6H_5$ | $-NH-CH_3$ | $C_{16}H_{16}N_4O_2S$ | 17.1 | 17.8 |
| 431. | $-NH-$(carbazol-3-yl) | $-NH-$(carbazol-3-yl) | $C_{33}H_{25}N_7$ | 18.9 | 18.5 |
| 432. | $-NH-$(9-ethylcarbazol-3-yl) | $-Cl$ | $C_{23}H_{20}ClN_5$ | 17.5 | 17.9 |
| 433. | $-NH-$(9-ethylcarbazol-3-yl) | $-OCH_3$ | $C_{24}H_{23}N_5O$ | 17.6 | 17.0 |
| 434. | $-NH-$(9-ethylcarbazol-3-yl) | $-N(CH_3)_2$ | $C_{25}H_{26}N_6$ | 20.5 | 21.2 |
| 435. | " | $-NH-$(9-ethylcarbazol-3-yl) | $C_{37}H_{33}N_7$ | 17.0 | 17.2 |

-continued

| No. | Z₁ | Z₂ | Empirical Formula | Cal'd. N% | Found N% |
|---|---|---|---|---|---|
| 436. | -NH-carbazole-N-C₃H₇(n) | -NH-carbazole-N-C₃H₇(n) | $C_{39}H_{37}N_7$ | 16.3 | 16.6 |
| 437. | -NH-carbazole-N-CH₂CH₂N(CH₃)₂ | —OCH₃ | $C_{26}H_{28}N_6O$ | 19.1 | 19.8 |
| 438. | " | —NH—CH₃ | $C_{26}H_{29}N_7$ | 22.3 | 22.5 |
| 439. | " | -NH-carbazole-N-CH₂CH₂N(CH₃)₂ | $C_{41}H_{43}N_9$ | 19.1 | 19.8 |
| 440. | -NH-carbazole-NH | -NH-carbazole-NH | $C_{33}H_{25}N_7$ | 18.9 | 18.1 |
| 441. | -NH-dibenzofuran | —Cl | $C_{21}H_{15}ClN_4O$ | 15.0 | 15.4 |
| 442. | " | —OC₂H₅ | $C_{23}H_{20}N_4O_2$ | 14.5 | 15.0 |
| 443. | " | -NH-dibenzofuran | $C_{33}H_{23}N_5O_2$ | 13.4 | 13.7 |
| 444. | -NH-dibenzothiophene | -NH-dibenzothiophene | $C_{33}H_{23}N_5S_2$ | 12.7 | 12.5 |

In the following table are presented further pyridine compounds prepared in accordance with the process of this invention:

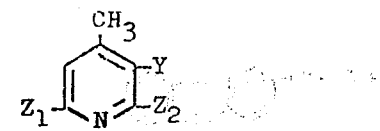

or tautomeric forms.

| No. | Y | Z₁ | Z₂ | Empirical Formula | Cal'd. N% | Found N% |
|---|---|---|---|---|---|---|
| 445. | —H | —NH₂ | —Cl | $C_6H_7N_2Cl$ | 20.1 | 20.7 |
| 446. | " | " | —NH₂ | $C_6H_9N_3$ | 34.1 | 33.6 |
| 447. | " | " | —OH | $C_6H_8N_2O$ | 22.6 | 22.8 |
| 448. | " | " | —OCH₃ | $C_7H_{10}N_2O$ | 20.3 | 20.1 |
| 449. | " | " | —SC₂H₅ | $C_8H_{12}N_2S$ | 16.6 | 17.1 |
| 450. | " | " | —SO₂—CH₃ | $C_7H_{10}N_2O_2S$ | 15.0 | 15.2 |
| 451. | " | " | —NH—CH₃ | $C_7H_{11}N_3$ | 30.6 | 31.0 |
| 452. | " | —NH—CH₃ | " | $C_8H_{13}N_3$ | 27.8 | 28.2 |
| 453. | " | —NHCH₂CH₂OH | —NHCH₂CH₂OH | $C_{10}H_{17}N_3O_2$ | 19.9 | 20.2 |
| 454. | " | —N(C₂H₅)₂ | —N(C₂H₅)₂ | $C_{14}H_{25}N_3$ | 17.9 | 17.3 |

-continued

| No. | Y | $Z_1$ | $Z_2$ | Empirical Formula | Cal'd. N% | Found N% |
|---|---|---|---|---|---|---|
| 455. | '' | —N(morpholine) | —N(morpholine) | $C_{14}H_{21}N_3O_2$ | 16.0 | 16.3 |
| 456. | '' | —NHCH$_2$CH$_2$CH$_3$ | —NHCH$_2$CH$_2$N(CH$_3$)$_2$ | $C_{13}H_{23}N_4$ | 23.8 | 23.2 |
| 457. | —NH$_2$ | —NH$_2$ | —NH$_2$ | $C_6H_{10}N_4$ | 40.6 | 40.8 |
| 458. | '' | —NH—CH$_3$ | —NH—CH$_3$ | $C_8H_{14}N_4$ | 33.7 | 33.2 |
| 459. | '' | —N(CH$_3$)$_2$ | —N(CH$_3$)$_2$ | $C_{10}H_{18}N_4$ | 28.9 | 28.7 |
| 460. | '' | —NHCH$_2$CH$_2$OH | —NHCH$_2$CH$_2$OH | $C_{10}H_{18}N_4O_2$ | 24.8 | 25.1 |
| 461. | —NO | —NH—CH$_3$ | —NH—CH$_3$ | $C_8H_{12}N_4O$ | 31.1 | 31.0 |
| 462. | '' | —N(CH$_3$)$_2$ | —N(CH$_3$)$_2$ | $C_{10}H_{16}N_4O$ | 26.9 | 26.7 |
| 463. | '' | —N(morpholine) | —N(morpholine) | $C_{14}H_{20}N_4O_3$ | 19.2 | 19.5 |
| 464. | —NO$_2$ | —NH—CH$_3$ | —NH—CH$_3$ | $C_8H_{12}N_4O_2$ | 28.5 | 28.5 |
| 465. | '' | —N(CH$_3$)$_2$ | —N(CH$_3$)$_2$ | $C_{10}H_{16}N_4O_2$ | 25.0 | 25.3 |
| 466. | '' | —N(morpholine) | —N(morpholine) | $C_{14}H_{20}N_4O_4$ | 18.2 | 18.5 |
| 467. | —CH$_3$ | —NH—CH$_3$ | —NH—CH$_3$ | $C_9H_{15}N_3$ | 25.4 | 26.0 |
| 468. | —CH$_2$—CH$_3$ | —NH—CH$_3$ | —NH—CH$_2$—CH$_3$ | $C_{11}H_{19}N_3$ | 21.7 | 22.0 |
| 469. | —CH$_2$CH$_2$CN | —NH$_2$ | —NH$_2$ | $C_9H_{12}N_4$ | 31.8 | 32.0 |
| 470. | —CH$_2$CH$_2$O—Ph | '' | '' | $C_{15}H_{17}N_3O$ | 16.5 | 17.0 |
| 471. | —CH$_2$CH$_2$N(C$_2$H$_5$)—OC$_6$H$_5$ | —NH—CH$_3$ | —NH—CH$_3$ | $C_{19}H_{26}N_4O$ | 17.2 | 17.5 |
| 472. | —CH$_2$CH$_2$N(C$_2$H$_5$)$_2$ | '' | —OCH$_2$CH=CH$_2$ | $C_{16}H_{27}N_3O$ | 15.2 | 15.3 |
| 473. | —CH$_2$—CH=CH$_2$ | '' | —NH—CH$_3$ | $C_{11}H_{17}N_3$ | 22.0 | 22.4 |
| 474. | —CH$_2$—C(CH$_3$)=CH$_2$ | '' | —SO$_2$CH$_2$CH=CH$_2$ | $C_{14}H_{20}N_2O_2S$ | 10.0 | 9.8 |
| 475. | —C$_3$H$_7$(n) | —NHCH$_2$CH$_3$ | | $C_{15}H_{27}N_3$ | 16.8 | 16.5 |
| 476. | —C$_4$H$_9$(n) | —NH—CH$_3$ | —O—(cyclohexyl) | $C_{17}H_{28}N_2O$ | 10.1 | 9.7 |
| 477. | —C$_4$H$_9$(iso) | '' | —O—CH$_2$—Ph | $C_{18}H_{24}N_2O$ | 9.9 | 10.2 |
| 478. | —C$_6$H$_{13}$(n) | —NH—CH$_3$ | —O—C$_6$H$_4$—CH$_3$ | $C_{18}H_{24}N_2O$ | 9.9 | 10.4 |
| 479. | —C$_6$H$_{10}$—CH$_3$ (cyclohexyl) | —NH—C$_3$H$_7$(iso) | —OCH$_2$CH$_2$OCH$_3$ | $C_{19}H_{32}N_2O$ | 9.4 | 9.5 |
| 480. | —CH$_2$—Ph | —NH—CH$_3$ | —NHCH$_2$CH$_2$CH$_2$N(CH$_3$)$_2$ | $C_{19}H_{27}N_4$ | 18.0 | 18.3 |
| 481. | —Ph | —NH$_2$ | —O—CH$_2$—C(CH$_3$)=CH$_2$ | $C_{16}H_{18}N_2O$ | 11.0 | 10.5 |
| 482. | —C$_6$H$_4$—OCH$_3$ (o) | '' | —S—CH(CH$_3$)$_2$ | $C_{16}H_{20}N_2OS$ | 9.7 | 9.5 |
| 483. | —C$_6$H$_3$(Cl)(CH$_3$) | —NH—CH$_3$ | —S—Ph | $C_{20}H_{19}ClN_2S$ | 7.9 | 8.3 |

-continued

| No. | Y | Z₁ | Z₂ | Empirical Formula | Cal'd. N% | Found N% |
|---|---|---|---|---|---|---|
| 484. | 2,5-dimethyl-4-chlorophenyl (CH₃, Cl, CH₃ substituted) | " | $-S-C_6H_4-Cl$ | $C_{21}H_{20}Cl_2N_2S$ | 6.9 | 6.8 |
| 485. | $-CH_2CH_2-N(morpholino)$ | $-NH_2$ | $-NH_2$ | $C_{12}H_{20}N_4O$ | 23.7 | 23.9 |
| 486. | " | $-N(CH_3)_2$ | $-N(CH_3)_2$ | $C_{16}H_{28}N_4O$ | 19.2 | 19.7 |
| 487. | $-CH_2CH_2-N(piperidino)$ | $-NH-CH_3$ | $-NH-CH_3$ | $C_{15}H_{26}N_4$ | 21.4 | 21.6 |
| 488. | $-CH_2CH_2-N(pyrrolidino)$ | " | " | $C_{14}H_{24}N_4$ | 22.6 | 22.2 |
| 489. | $-COOCH_3$ | " | " | $C_{10}H_{15}N_3O_2$ | 20.1 | 20.3 |
| 490. | $-COOC_2H_5$ | " | " | $C_{11}H_{17}N_3O_2$ | 18.8 | 18.5 |
| 491. | " | $-N(C_2H_5)_2$ | $-N(C_2H_5)_2$ | $C_{17}H_{29}N_3O_2$ | 13.7 | 14.0 |
| 492. | " | $-N(morpholino)$ | $-NH-CH_3$ | $C_{14}H_{21}N_3O_3$ | 15.0 | 14.8 |
| 493. | $-COOC_4H_9(n)$ | $-NHCH_2CH_2OH$ | | $C_{15}H_{25}N_3O_4$ | 13.5 | 13.8 |
| 494. | $-COOC_6H_{13}(n)$ | $-NHCH_2CH_2CH_3$ | $-NHCH_2CH_2N(CH_3)_2$ | $C_{20}H_{36}N_4O_2$ | 15.4 | 15.0 |
| 495. | $-COCH_3$ | $-NH-CH_3$ | $-NH-CH_3$ | $C_{10}H_{15}N_3O$ | 21.7 | 21.5 |
| 496. | $-CO-CH=CH_2$ | " | " | $C_{11}H_{15}N_3O$ | 20.5 | 20.7 |
| 497. | $-CO-C_6H_{13}(n)$ | $-NH-CH_3$ | $-N(CH_3)_2$ | $C_{16}H_{27}N_3O$ | 15.2 | 15.3 |
| 498. | $-CO-$cyclohexyl | " | " | $C_{16}H_{25}N_3O$ | 15.3 | 15.5 |
| 499. | $-CO-CH_2-C_6H_5$ | " | $-NH-CH_3$ | $C_{16}H_{19}N_3O$ | 15.6 | 15.8 |
| 500. | $-CO-C_6H_5$ | $-NH_2$ | $-NH_2$ | $C_{13}H_{13}N_3O$ | 18.5 | 18.3 |
| 501. | " | $-NH-CH_3$ | $-NH-CH_3$ | $C_{15}H_{17}N_3O$ | 16.5 | 16.7 |
| 502. | " | $-N(CH_3)_2$ | $-N(CH_3)_2$ | $C_{17}H_{21}N_3O$ | 14.8 | 14.6 |
| 503. | " | $-NH-CH_3$ | $-N(morpholino)$ | $C_{16}H_{21}N_3O_2$ | 13.5 | 13.2 |
| 504. | $-CO-NH_2$ | $-NH_2$ | $-Cl$ | $C_7H_8ClN_3O$ | 22.6 | 22.8 |
| 505. | " | " | $-NH_2$ | $C_7H_{10}N_4O$ | 33.8 | 34.2 |
| 506. | $-CO-NH_2$ | $-NH_2$ | $-OH$ | $C_7H_9N_3O_2$ | 25.1 | 24.7 |
| 507. | $-CO-NH_2$ | $-NH_2$ | $-OC_2H_5$ | $C_9H_{13}N_3O_2$ | 21.5 | 22.1 |
| 508. | " | " | $-SC_2H_5$ | $C_9H_{13}N_3OS$ | 19.9 | 19.6 |
| 509. | " | " | $-SO_2C_2H_5$ | $C_9H_{13}N_3O_3S$ | 17.3 | 17.5 |
| 510. | " | $-NH-CH_3$ | $-NH-CH_3$ | $C_9H_{14}N_4O$ | 28.9 | 28.7 |
| 511. | " | $-NHCH_2CH_2OCH_3$ | | $C_{13}H_{22}N_4O_3$ | 19.9 | 19.6 |
| 512. | " | $-N(C_2H_5)_2$ | $-N(C_2H_5)_2$ | $C_{15}H_{28}N_4O$ | 20.1 | 20.5 |
| 513. | " | $-NHCH_2CH_3$ | $-N(morpholino)$ | $C_{13}H_{20}N_4O_2$ | 21.2 | 21.4 |
| 514. | " | " | $-NHCH_2CH_2CH_2N(CH_3)_2$ | $C_{14}H_{25}N_5O$ | 25.1 | 25.3 |
| 515. | $-CO-NH-CH_3$ | $-NH_2$ | $-NH_2$ | $C_8H_{12}N_4O$ | 31.1 | 31.0 |
| 516. | $-CONHCH_2CH_2OH$ | $-NH_2$ | $-S-CH_2-CH=CH_2$ | $C_{12}H_{17}N_3O_3$ | 16.7 | 17.0 |
| 517. | $-CONHC_4H_9(n)$ | $-NH-CH_3$ | $-NH-CH_3$ | $C_{13}H_{23}N_4O$ | 22.4 | 22.1 |
| 518. | $-CO-N(CH_2)_2$ (aziridinyl) | $-NHCH_2CH_2OCH_3$ | $-NHCH_2CH_2OCH_3$ | $C_{15}H_{24}N_4O_3$ | 18.2 | 18.6 |
| 519. | $-CO-N(C_2H_5)_2$ | $-N(C_2H_5)_2$ | $-N(C_2H_5)_2$ | $C_{19}H_{34}N_4O$ | 16.8 | 17.1 |

-continued

| No. | Y | $Z_1$ | $Z_2$ | Empirical Formula | Cal'd. N% | Found N% |
|---|---|---|---|---|---|---|
| 520. | -CO-N(morpholino, H,O) | -NH-CH$_3$ | -NH-C$_3$H$_7$(iso) | $C_{15}H_{24}N_4O_2$ | 19.2 | 19.1 |
| 521. | -CO-NH-phenyl | -NH$_2$ | -NH$_2$ | $C_{13}H_{14}N_4O$ | 23.2 | 23.6 |
| 522. | " | -NH-CH$_3$ | -NH-CH$_3$ | $C_{15}H_{18}N_4O$ | 20.7 | 20.9 |
| 523. | -CO-NH-(2,5-dimethylphenyl) | -NHCH$_2$CH$_2$OH | -NHCH$_2$CH$_2$OH | $C_{19}H_{26}N_4O_3$ | 15.7 | 16.2 |
| 524. | -CO-N(CH$_3$)(phenyl) | -NH-CH$_3$ | -NH-CH$_3$ | $C_{16}H_{20}N_4O$ | 19.7 | 19.5 |
| 525. | -SO$_2$-CH$_2$-CH$_3$ | " | -NH-CH$_2$-CH$_3$ | $C_{11}H_{19}N_3O_3S$ | 15.4 | 15.2 |
| 526. | -SO$_2$-C$_3$H$_7$(n) | -NH-C$_3$H$_7$(n) | | $C_{15}H_{27}N_3O_3S$ | 12.8 | 13.1 |
| 527. | -SO$_2$-C$_4$H$_9$(n) | -NH$_2$ | -NH$_2$ | $C_{10}H_{17}N_3O_2S$ | 17.3 | 17.6 |
| 528. | -SO$_2$-C$_4$H$_9$(iso) | " | " | | 17.3 | 17.4 |
| 529. | -SO$_2$-C$_5$H$_{11}$(iso) | -NH-CH$_3$ | -N(CH$_3$)$_2$ | $C_{14}H_{25}N_3O_2S$ | 14.0 | 14.3 |
| 530. | -SO$_2$-cyclohexyl | " | " | $C_{15}H_{25}N_3O_2S$ | 13.5 | 14.0 |
| 531. | -SO$_2$-phenyl | " | -NH-CH$_3$ | $C_{14}H_{17}N_3O_2S$ | 14.4 | 14.2 |
| 532. | -SO$_2$-(4-Cl-phenyl) | -NHCH$_2$CH$_2$OH | -NH-CH$_3$ | $C_{15}H_{18}ClN_3O_3S$ | 11.8 | 12.2 |
| 533. | -SO$_2$-(2,5-dimethylphenyl) | -N(morpholino) | " | $C_{19}H_{25}N_3O_3S$ | 11.2 | 11.4 |
| 534. | -SO$_2$-NH$_2$ | -NH$_2$ | -NH$_2$ | $C_8H_{10}N_4O_2S$ | 27.7 | 27.5 |
| 535. | -SO$_2$-NH$_2$ | -NH$_2$ | -SO$_2$-cyclohexyl | $C_{12}H_{13}N_3O_4S_2$ | 12.8 | 13.2 |
| 536. | " | -NH-CH$_3$ | -NH-CH$_3$ | $C_8H_{14}N_4O_2S$ | 24.4 | 24.2 |
| 537. | " | -NHCH$_2$CH$_2$OH | -NHCH$_2$CH$_2$OH | $C_{10}H_{18}N_4O_4S$ | 19.3 | 19.5 |
| 538. | -SO$_2$-N(CH$_3$)$_2$ | -NH-phenyl | -NH-phenyl | $C_{20}H_{22}N_4O_2S$ | 14.7 | 15.2 |
| 539. | -SO$_2$NHC$_2$H$_5$ | -NH-CH$_3$ | -S-cyclohexyl | $C_{15}H_{25}N_3O_2S_2$ | 12.2 | 12.4 |
| 540. | -SO$_2$NH(CH$_2$)$_3$OCH$_3$ | -NH$_2$ | -NH-N(CH$_3$)$_2$ | $C_{12}H_{23}N_5O_3S$ | 22.1 | 22.5 |
| 541. | -SO$_2$-N(morpholino) | " | -NH$_2$ | $C_{10}H_{16}N_4O_3S$ | 20.6 | 21.1 |
| 542. | " | -NH-CH$_3$ | -N(morpholino) | $C_{15}H_{24}N_4O_4S$ | 15.7 | 16.0 |
| 543. | " | -N(C$_2$H$_5$)$_2$ | -N(C$_2$H$_5$)$_2$ | $C_{18}H_{32}N_4O_3S$ | 14.6 | 14.8 |

-continued

| No. | Y | $Z_1$ | $Z_2$ | Empirical Formula | Cal'd N% | Found N% |
|---|---|---|---|---|---|---|
| 544. | $-SO_2-N\text{(piperidine)}$ | $-NH-CH_3$ | $-NH-CH_3$ | $C_{13}H_{22}N_4O_2S$ | 18.8 | 18.5 |
| 545. | " | " | $-S-CH_2-\text{phenyl}$ | $C_{19}H_{25}N_3O_2S_2$ | 10.7 | 11.2 |
| 546. | $-SO_2-N\text{(piperazine)}N-CH_3$ | " | $-NH-CH_3$ | $C_{12}H_{23}N_5O_2S$ | 23.2 | 23.0 |
| 547. | $-SO_2-NH-\text{cyclohexyl}$ | " | " | $C_{14}H_{24}N_4O_2S$ | 17.9 | 18.2 |
| 548. | " | " | $-SO_2-\text{cyclohexyl}$ | $C_{19}H_{31}N_3O_4S_2$ | 9.8 | 10.2 |
| 549. | $-SO_2NHCH_2-\text{phenyl}$ | $-N\text{(morpholine)}O$ | $-NHCH_2CH_2OH$ | $C_{19}H_{26}N_4O_4S$ | 13.8 | 13.5 |
| 550. | $-SO_2-NH-\text{phenyl}$ | $-NH_2$ | $-NH_2$ | $C_{12}H_{14}N_4O_2S$ | 20.1 | 20.3 |
| 551. | " | $-NH-\text{cyclohexyl}$ | $-NH-\text{cyclohexyl}$ | $C_{24}H_{34}N_4O_2S$ | 12.7 | 12.5 |
| 552. | " | $-NH-CH_2-\text{phenyl}$ | $-NH-CH_2-\text{phenyl}$ | $C_{26}H_{26}N_4O_2S$ | 12.2 | 12.5 |
| 553. | $-SO_2-NH-\text{phenyl}$ | $-NH-\text{phenyl}$ | $-NH-\text{phenyl}$ | $C_{24}H_{22}N_4O_2S$ | 13.0 | 13.2 |
| 554. | " | $-NH-\text{naphthyl}$ | $-NH-\text{naphthyl}$ | $C_{32}H_{26}N_4O_2S$ | 10.6 | 10.2 |
| 555. | $-OC-\text{(furan)}$ | $-NH-CH_3$ | $-OCH_2\overset{CH_3}{\underset{}{C}}=CH_2$ | $C_{16}H_{18}N_2O_3$ | 9.8 | 9.5 |
| 556. | " | " | $-NH(CH_2)_3-N(CH_3)_2$ | $C_{17}H_{24}N_4O_2$ | 17.8 | 18.2 |
| 557. | $-OC-\text{(thiophene)}$ | " | $-O-\text{cyclohexyl}-CH_3$ | $C_{19}H_{24}N_2O_3$ | 8.5 | 9.0 |
| 558. | $-OC-\text{(pyridine)}$ | $-NH_2$ | $-NH_2$ | $C_{12}H_{12}N_4O$ | 24.5 | 25.0 |
| 559. | " | $-NH-CH_3$ | $-NH-CH_3$ | $C_{14}H_{16}N_4O$ | 21.8 | 22.2 |
| 560. | " | $-N(CH_3)_2$ | $-N(CH_3)_2$ | $C_{16}H_{20}N_4O$ | 19.7 | 20.1 |
| 561. | $-\text{benzimidazole}-CO-$ | $-NH-CH_3$ | $-NH-CH_3$ | $C_{16}H_{17}N_5O$ | 23.7 | 23.5 |
| 562. | " | $-N(CH_3)_2$ | $-N(CH_3)_2$ | $C_{18}H_{21}N_5O$ | 21.7 | 21.5 |

-continued-

| No. | Y | $Z_1$ | $Z_2$ | Empirical Formula | Cal'd. N% | Found N% |
|---|---|---|---|---|---|---|
| 563. | 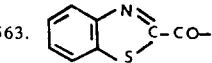 | —NH—CH₃ | —NH—CH₃ | $C_{16}H_{16}N_4OS$ | 17.9 | 18.2 |
| 564. | 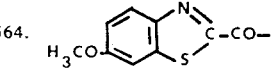 | —N(CH₃)₂ | —N(CH₃)₂ | $C_{19}H_{22}N_4O_2S$ | 15.1 | 15.5 |
| 565. | 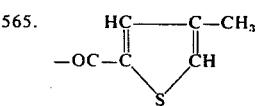 | —NH—CH₃ | —O—CH₂—C₆H₄—Cl | $C_{20}H_{19}ClN_2O_2S$ | 7.3 | 7.0 |
| 566. |  | —NH—CH₃ | —NH—CH₃ | $C_{14}H_{18}N_4$ | 23.1 | 23.5 |
| 567. | 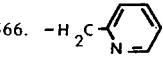 | " | " | " | 23.1 | 23.3 |
| 568. | 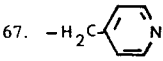 | " | " | $C_{15}H_{20}N_4$ | 21.9 | 21.7 |
| 569. | —C₄H₉(n) | —CN | —N(CH₃)₂ | $C_{13}H_{19}N_3$ | 19.4 | 19.0 |
| 570. | —CO—NH₂ | —OCH₃ | —OCH₃ | $C_9H_{12}N_2O_3$ | 14.3 | 14.7 |
| 571. | —CO—CH₃ | —OC₂H₅ | —OC₂H₅ | $C_{12}H_{17}NO_3$ | 6.7 | 6.5 |

In the following table are presented further pyridine compounds prepared in accordance with the method of this invention:

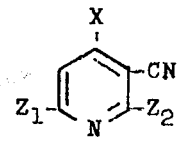

or tautomeric forms.

| No. | Y | $Z_1$ | $Z_2$ | Empirical Formula | Cal'd. N% | Found N% |
|---|---|---|---|---|---|---|
| 572. | —H | —NH—CH₃ | —NH—CH₃ | $C_8H_{10}N_4$ | 34.6 | 25.0 |
| 573. | —H | | —NH—CH₂CH₂—OH | $C_{10}H_{14}N_4O_2$ | 25.2 | 25.0 |
| 574. | —C₃H₇(n) | —NHCH₂CH₂CH₃ | —NH(CH₂)₃N(CH₃)₂ | $C_{17}H_{29}N_5$ | 23.1 | 23.3 |
| 575. | —C₃H₇(iso) | —NHCH₂CH₂CH₃ | —NH(CH₂)₃H(CH₃)₂ | $C_{17}H_{29}N_5$ | 23.1 | 22.8 |
| 576. | —C₆H₁₃(n) | | —NHCH₂CH₂CH₂OCH₃ | $C_{20}H_{34}N_4O_2$ | 15.5 | 16.0 |
| 577. | —CH₂CH₂N(CH₃)₂ | —NH—CH₃ | —NH—CH₃ | $C_{12}H_{19}N_5$ | 30.0 | 30.3 |
| 578. | —CH₂CH₂N(CO—CH₃)(CH₃) | —NH—CH₃ | —NH—CH₃ | $C_{13}H_{19}N_5O$ | 26.8 | 27.0 |
| 579. | —CH₂CH₂—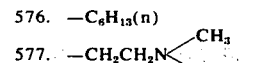 | —NH₂ | —NH₂ | $C_{12}H_{17}N_5O$ | 28.3 | 28.8 |
| 580. | —CH₂CH₂—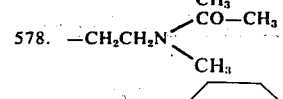 | —NH₂ | —NH₂ | $C_{12}H_{17}N_5$ | 30.3 | 30.5 |
| 581. | —CH₂CH₂OH | —NH—CH₃ | —NH—CH₃ | $C_{10}H_{14}N_4O$ | 27.2 | 27.5 |
| 582. | —CH₂CH₂O—COCH₃ | —NHCH₂CH₂CH₂OH | | $C_{16}H_{24}N_4O_4$ | 16.7 | 17.0 |
| 583. | —(CH₂)₂O—CONHC₂H₅ | —NH—CH₃ | —NH—CH₃ | $C_{13}H_{19}N_5O_2$ | 25.3 | 25.1 |
| 584. | —CH₂CH₂O—C₆H₅ | | —NH(CH₂)₃O—C₃H₇(iso) | $C_{26}H_{38}N_4O_3$ | 12.3 | 12.7 |
| 585. | 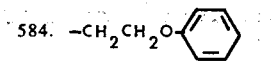 | —NH₂ | —NH₂ | $C_{12}H_{16}N_4$ | 25.9 | 25.5 |

-continued

| No. | Y | $Z_1$ | $Z_2$ | Empirical Formula | Cal'd. N% | Found N% |
|---|---|---|---|---|---|---|
| 586. | $-CH_2$-C₆H₅ | $-NH_2$ | $-NH_2$ | $C_{13}H_{12}N_4$ | 25.0 | 25.3 |
| 587. | C₆H₅ | morpholino | $-NH-CH_3$ | $C_{17}H_{18}N_4$ | 20.1 | 20.7 |
| 588. | 4-Cl-C₆H₄ | $-NH-CH_3$ | $-NH-CH_3$ | $C_{14}H_{13}N_4Cl$ | 20.6 | 21.0 |
| 589. | 2,6-(CH₃)₂-C₆H₃ | $-NH-CH_3$ | $-NH-CH_3$ | $C_{16}H_{18}N_4$ | 21.0 | 20.4 |
| 590. | 2-furyl | $-NH-CH_3$ | $-NH-CH_3$ | $C_{12}H_{12}N_4O$ | 24.5 | 24.7 |
| 591. | 2-thienyl | $-NH-CH_3$ | $-NH-CH_3$ | $C_{12}H_{12}N_4S$ | 22.9 | 22.5 |
| 592. | 2-thiazolyl | $-NH-CH_3$ | $-NH-CH_3$ | $C_{11}H_{11}N_5S$ | 28.6 | 28.5 |
| 593. | $-CH_2$-(2-pyridyl) | $-NH-CH_3$ | $-NH-CH_3$ | $C_{14}H_{15}N_5$ | 27.7 | 28.2 |
| 594. | 2-pyridyl | $-NH-CH_3$ | $-NH-CH_3$ | $C_{13}H_{13}N_5$ | 28.3 | 28.7 |
| 595. | 2-benzimidazolyl | $-NH-CH_3$ | $-NH-CH_3$ | $C_{15}H_{14}N_6$ | 30.2 | 29.6 |
| 596. | $-H_2C-C$(thiazolyl) | $-NH-CH_3$ | $-NH-CH_3$ | $C_{12}H_{13}N_5S$ | 27.0 | 27.3 |
| 597. | 2-benzimidazolyl | $-NH-C_2H_5$ | $-NH-C_2H_5$ | $C_{17}H_{18}N_6$ | 27.5 | 27.7 |
| 598. | $-C_3H_7(n)$ | $-CN$ | $-N(CH_3)_2$ | $C_{12}H_{14}N_4$ | 26.2 | 26.5 |
| 599. | $-C_3H_7(n)$ | $-SCH_3$ | $-OCH_3$ | $C_{11}H_{14}N_2OS$ | 12.6 | 13.0 |

In the following table are presented further pyridine compounds prepared in accordance with the method of this invention:

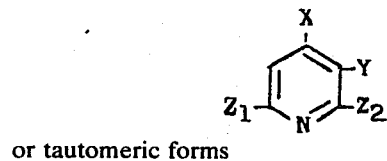

or tautomeric forms

| No. | X | Y | $Z_1$ | $Z_2$ | Empirical Formula | Cal'd. N% | Found N% |
|---|---|---|---|---|---|---|---|
| 600. | $-C_3H_7(n)$ | $-C_4H_9(n)$ | $-CN$ | $-N(CH_3)_2$ | $C_{15}H_{23}N_3$ | 17.1 | 17.5 |
| 601. | $-C_3H_7(n)$ | $-CN$ | $-OCH_3$ | '' | $C_{12}H_{17}N_3O$ | 18.7 | 19.2 |
| 602. | $-C_3H_7(n)$ | $-C_3H_7(n)$ | $-SCH_3$ | $-SCH_3$ | $C_{13}H_{21}NS_2$ | 5.5 | 5.8 |
| 603. | H | $-CH_3$ | $-NH_2$ | $-NH_2$ | $C_6H_9N_3$ | 34.1 | 34.5 |

-continued

| No. | X | Y | Z₁ | Z₂ | Empirical Formula | Cal'd. N% | Found N% |
|---|---|---|---|---|---|---|---|
| 604. | H | -CH₂-(2-pyridyl) | -NH-CH₃ | -NH-CH₃ | C₁₃H₁₆N₄ | 24.5 | 24.2 |
| 605. | H | -CO-NH₂ | -N(CH₃)₂ | -N(CH₃)CH(CH₃)₂ | C₁₀H₁₆N₄O | 26.9 | 27.3 |
| 606. | -C₂H₅ | -NH₂ | -NH-CH₃ | -OCH₂C=CH₂ | C₁₂H₁₉N₃O | 19.0 | 19.2 |
| 607. | -C₂H₅ | -H | -NHCH₂CH₂OH | -N(morpholino) | C₁₃H₂₁N₃O | 17.9 | 18.2 |
| 608. | -C₄H₉(n) | -NO | -NH-CH₃ | -NH-CH₃ | C₁₁H₁₈N₄O | 25.2 | 25.0 |
| 609. | -C₄H₉(n) | -NO₂ | -NH-CH₃ | -NH-CH₃ | C₁₁H₁₈N₄O₂ | 23.5 | 23.2 |
| 610. | -C₄H₉(n) | -C₄H₉(n) | -NH₂ | -O-C₆H₄-OCH₃ | C₂₀H₂₈N₂O₂ | 8.5 | 8.2 |
| 611. | -C₄H₉(sec) | -CH₂-(pyridyl) | -NH-C₂H₅ | | C₁₉H₂₈N₄ | 17.9 | 17.6 |
| 612. | -C₄H₉(sec) | (thiazolyl) | -N(C₂H₅)₂ | -N(C₂H₅)₂ | C₂₀H₃₂N₄S | 15.5 | 16.1 |
| 613. | -C₄H₉(iso) | -OC-(pyridyl) | -NHCH₂CH₂OCH₃ | | C₂₁H₃₀N₄O₃ | 14.5 | 14.2 |
| 614. | -C₄H₉(tert) | -CO-NH₂ | -NH-CH₃ | -SO₂CH₂CH₂OCH₃ | C₁₄H₂₃N₃O₄S | 12.8 | 12.2 |
| 615. | -C₅H₁₁(iso) | -CO-NH₂ | -NH-CH₃ | -SO₂-C₆H₄-CN | C₁₉H₂₂N₄O₃S | 14.5 | 14.3 |
| 616. | -CH=CH₂ | -COOC₂H₅ | -N(morpholino) | -N(CH₃)₂ | C₁₆H₂₃N₃O₃ | 13.8 | 14.2 |
| 617. | -CH=CH-CH₃ | -SO₂NH₂ | | -NH-C₆H₅ | C₂₀H₂₀N₄O₂S | 14.7 | 15.2 |
| 618. | -CH₂CH₂N(C₂H₅)₂ | -CH₃ | -NH-CH₃ | -NH-CH₃ | C₁₄H₂₆N₄ | 22.4 | 22.8 |
| 619. | -CH₂CH₂CN | -CH₂CH₂N(CH₃)₂ | -N(morpholino) | -NH-CH₃ | C₁₇H₂₇N₅O | 22.1 | 22.5 |
| 620. | -CH₂CH₂OCH₃ | -CO-CH₃ | -NHCH₂CH₂CH₃ | -SCH₂CH₂OCH₃ | C₁₆H₂₆N₂O₃S | 8.6 | 8.9 |
| 621. | -CH₂CH₂-N(piperidino) | -H | -NH(CH₂)₃-OCH₃ | -NH(CH₂)₃-OCH₃ | C₂₀H₃₆N₄O₂ | 15.4 | 15.6 |
| 622. | -CH₂CH₂-N(piperidino) | -CO-NH₂ | | -N(C₂H₅)₂ | C₂₁H₃₇N₅O | 18.7 | 18.5 |
| 623. | -C₆H₁₁ | -CH₂-OCH₃ | -NH₂ | -NH₂ | C₁₃H₂₁N₃O | 17.9 | 17.6 |
| 624. | -C₆H₅ | -H | -NH-C₆H₅ | | C₂₃H₁₉N₃ | 12.5 | 12.7 |
| 625. | " | -CO-NH₂ | -N(CH₃)₂ | -SO₂-C₆H₃(CH₃)₂ | C₂₂H₂₃N₃O₃S | 10.3 | 10.7 |
| 626. | " | -CO-CH₃ | " | -SO₂CH₂-C₆H₄-CN | C₂₃H₂₁N₃O₂S | 10.4 | 10.6 |

-continued

| No. | X | Y | $Z_1$ | $Z_2$ | Empirical Formula | Cal'd. N% | Found N% |
|---|---|---|---|---|---|---|---|
| 627. |  | —H | —NH—CH$_3$ | —NH—CH$_3$ | $C_{12}H_{14}N_4$ | 26.2 | 26.8 |
| 628. | '' | —CO—NH$_2$ | —N(CH$_3$)CH$_3$ | —N(CH$_3$)CH$_3$ | $C_{15}H_{19}N_5O$ | 24.6 | 25.0 |
| 629. |  | —CO—NH$_2$ | —NHCH$_2$CH$_2$OCH$_3$ | | $C_{15}H_{21}N_5O_3S$ | 20.0 | 20.3 |
| 630. | 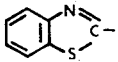 | —CO—NH$_2$ | —NH$_2$ | —OH | $C_{13}H_{10}N_4O_2S$ | 19.6 | 19.4 |

In those instances in the foregoing tables where only one value is presented for $Z_1$ and $Z_2$, this means that $Z_1$ and $Z_2$ are equal.

EXAMPLE 13

There are allowed to run 100 p.b.w. 3-methoxypropylamine into a suspension of 93.0 p.b.w. of 2,6-dichloro-3-cyano-4-methylpyridine in 200 p.b.w. ethyl alcohol for 2 hours at 20°C. This product is then agitated at room temperature for 18 hours. Then the resulting 2-chloro-3-cyano-4-methyl-6-(3'-methoxypropylamino)-pyridine of the formula

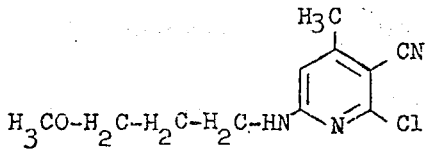

is drawn off, washed on the suction apparatus first with 120 p.b.w. ethyl alcohol and subsequently with water. The substance is analytically pure.

Analysis: $C_{11}H_{14}ClN_3O$. Calculated: 17.6% N 14.6% Cl. Found: 17.9% N 14.4% Cl.

EXAMPLE 14

Introduced into 1000 parts by weight methyl alcohol during cooling are 25.3 p.b.w. sodium. Added to this sodium methylate solution are 215 p.b.w. 2-chloro-3-cyano-4-methyl-6-(3'-methoxypropylamino)-pyridine, and subsequently the reaction solution is heated to the point of boiling for 24 hours under reflux. Then the methyl alcohol is distilled off and the residue stirred with water. The resulting 2-methoxy-3-cyano-4-methyl-6-(3'-methoxypropylamino)-pyridine of the formula

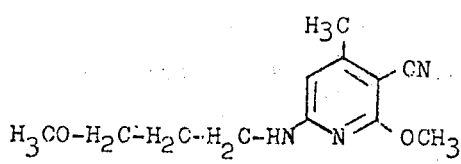

is an oil, which is isolated with ether. It may be purified by vacuum distillation.

Analysis: $C_{12}H_{17}N_3O_2$. Calculated: 17.9% N 26.4% -OCH$_3$. Found: 18.1% N 26.1% -OCH$_3$.

EXAMPLE 15 a. 13.8 p.b.w. 4-nitraniline are diazotized at 0° to +5°C. in 300 p.b.w. of water to which 36.0 p.b.w. hydrochloric acid of 30 % have been added, with a solution consisting of 7.7 p.b.w. sodium nitrite in 50 p.b.w. of water. The filtered diazo solution is allowed to run into a solution of 500 p.b.w. of water, 25.0 p.b.w. hydrochloric acid of 30 % and 32.2 p.b.w. 2,6-bis-(3'-methoxy-n.propylamino)-3-cyano-4-methyl-pyridine, whereby the reaction temperature is maintained during the coupling at 0° to +5°C. by the addition of 500 parts of ice. The pH valve of the batch is neutralized by the introduction of a solution of 65.2 p.b.w. sodium acetate in 200 p.b.w. of water, whereupon the coupling is quickly completed. The dyestuff being formed is then sucked off, washed with water until neutral and dried.

b. 1.0 g. of the dyestuff thus obtained which has the following formula

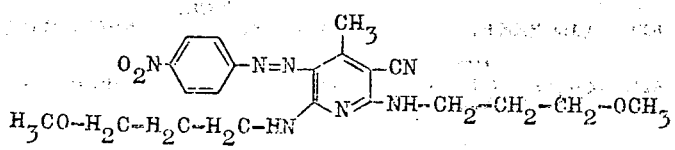

is finely dispersed and introduced while stirring into 2000 g. of water. This reaction mixture is adjusted to a pH value of 5 – 6 by the addition of acetic acid and then admixed with 4 g. ammonium sulfate and 2 g. of a commercial dispersing agent on the basis of a naphthalenesulfonic acid/formaldehyde condensation product. 100 g. of a polyester fabric on the basis of polyethylene glycolterephthalate are introduced into the dye liquor thus obtained and dyed for 1½ hours at 130°C. After subsequent rinsing, reductive aftertreatment with an alkaline sodium dithionite solution of 0.2 % during 15 minutes at 60° – 70°C., rinsing and drying, one obtains a deep reddish orange dyeing which shows very good fastness properties.

EXAMPLE 16 a. 16.3 p.b.w. 2-cyano-4-nitraniline are diazotized at 15°C. in 100 p.b.w. glacial acetic acid, with 34.2 p.b.w. nitrosylsulfuric acid of 41.3 %. The limpid diazo solution is then allowed to run into a suspension of 25.8 p.b.w. 2-methoxy-3-cyano-4-methyl-6-(3'-methoxy-propylamino)-pyridine and 66.0 g. sodium acetate in 160 p.b.w. ethanol. During the coupling the reaction temperature is maintained at 0° to +5°C. by cooling from the outside. When the coupling is completed, the dyestuff being formed is sucked off, washed first with ethanol, then with water and dried.

b. 30 p.b.w. of the dyestuff thus obtained (related to 1000 p.b.w. of the printing paste) which has the formula

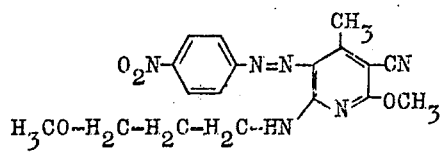

are incorporated in a finely dispersed form into a printing paste containing 45.0 p.b.w. carob bean meal, 6.0 p.b.w. 3-nitrobenzenesulfonic acid sodium and 3.0 p.b.w. citric acid. When this printing paste is applied onto a polyester fabric one obtains after printing, drying and setting on the thermosetting stenter during 45 seconds at 215°C., rinsing and working up as described in the above Example 15 b, a full reddish orange print which has very good fastness properties.

The dyestuff yields when printed into a triacete fabric and if it is employed in the form of the above printing paste and the printed fabric, after drying, is steamed for 10 minutes at a pressure of 2.5 atmospheres, rinsed, soaped, rinsed again and dried, a full reddish orange print having also very good fastness properties.

EXAMPLE 17 a. 29.7 g. 4-β-sulfatoethylsulfonyl-aniline-2-sulfonic acid are pasted up with 400 c.c. water, admixed with 25 c.c. 10 normal hydrochloric acid and diazotized by the addition of 100 c.c. 4 normal sodium dithionite solution. The reaction temperature is maintained at 0° to +3°C. by the addition of about 400 g. ice. The excess sodium, if any, is destroyed with little amidosulfonic acid and the diazo compound is added to a suspension of 14.8 g. 2.6-diamino-3-cyano-4-methyl-pyridine in 200 c.c. water to which 12.5 g. sodium bicarbonate have been added. The precipitated dyestuff is sucked off, and dried in vacuo. The reactive dye thus obtained has the following formula:

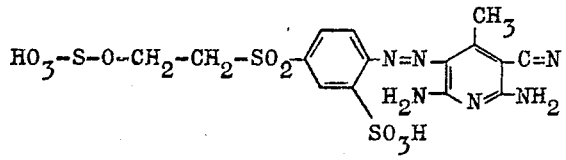

b. A mixture of mercerized or alkalized cotton is printed with the following printing paste:

| | |
|---|---|
| 50 g. | of the above dyestuff |
| 100 g. | urea |
| 370 g. | hot water |
| 450 g. | alginate thickener |
| 20 g. | sodium bicarbonate |
| 10 g. | sodium salt of the m-nitrobenzenesulfonic acid |
| 1000 g. | |

The print may be fixed either by steaming at 103° to 105°C. or by dry heating. In both cases the fabric is subsequently rinsed and soaped. The full greenish yellow print thus obtained has very good fastness properties.

Cationic azo dyes suited for dyeing and printing polyacrylonitrile and modifier polyester fibers may be prepared according to the following Example:

EXAMPLE 18 a. 4.57 p.b.w. 4'aminophenacyltrimethyl-ammonium chloride are dissolved in 20 p.b.w. of water and 7 p.b.w. concentrated hydrochloric acid, and diazotized at 0° – 5°C. with 4 p.b.w. 5 normal sodium nitrite solution. When the diazoltization is completed, 3.52 p.b.w. 3-cyano-4-methyl-2.6-bis-methylamino-pyridine, dissolved in 10 p.b.w. glacial acetic acid, are added to the diazo solution and the reaction mixture is stirred at a pH value of 3 – 5 until the coupling is completed.

The dyestuff is precipitated by the addition of sodium chloride of 10 %, sucked off and dried. It has the following formula:

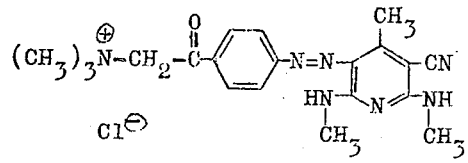

b. 1 g. of this dyestuff is pasted up with 2.5 g. acetic acid of 50 % and dissolved in 6 l. of water. To this dye liquor 1 g. sodium acetate and 10 g. sodium sulfate are added. Subsequently, 100 g. of a pre-washed polyacrylonitrile staple fiber yarn are introduced into the dye liquor which has a temperature of 60°C. This temperature is slowly raised to 100°C. and dyeing is carried out during 1 hour at boiling temperature. Subsequently, the temperature is lowered down to 70°C., the treated fabric is rinsed and dried. One obtains a clear deep orange dyeing with a very good fastness to light and to wetting, and a high absorption capacity.

c. 1 g. of the dyestuff is pasted up with 2 g. acetic acid of 50 % and dissolved in 5 l. of water which contains 1 g. sodium acetate. 100 g. of a pre-washed fabric of acid modified polyester fiber are then introduced at 60°C., the temperature is slowly raised and dyeing is carried out during 1 hour at 115°C. The temperature is then lowered down to 70°C. and the fabric is rinsed and dried. Obtained is a deep orange dyeing having a very good fastness to light and wetting.

Acid azo dyes which are suited for dyeing wool, silk and polyamide may be prepared according to the following Example:

EXAMPLE 19 a. 27.7 p.b.w. 4'-amino-azobenzene-4-sulfonic acid are diazotized in the usual manner and coupled in a slightly acid pH range with 23.6 p.b.w. 2.6-(β-hydroxyethylamino)-3-cyano-4-methyl-pyridine. The dyestuff being formed is salted out by the addition of sodium chloride of 10 %, sucked off and dried at 60°C. in vacuo. In the form of its free acid it corresponds to the following formula:

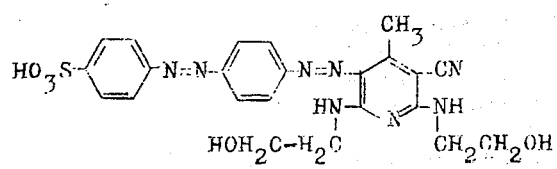

b. 1 g. of the above dyestuff is pasted up with 25 g. cold distilled water and dissolved in 975 g. boiling distilled water. The dyestuff solution is admixed with 2 g. acetic acid of 50 % and the reaction temperature is maintained at 60°C. At this temperature 100 g. of a pre-washed fabric of wool, silk or polyamide are introduced and the temperature is slowly raised to 100°C. and then maintained for 1 hour at boiling temperature. Subsequently, the temperature is lowered down to 70°C. and the fabric is rinsed and dried. Obtained is a deep yellowish red dyeing of high brilliancy and showing a very good fastness to light and to wetting.

We claim:

1. A compound of the formula

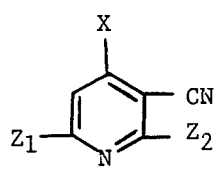

wherein X is alkyl having 1 to 6 carbon atoms, alkenyl having 2 to 6 carbon atoms, cycloalkyl having 3 to 8 carbon atoms, phenyl, benzyl, phenethyl, hydrogen, 2-dimethylaminoethyl, 2-diethylaminoethyl, 2-morpholinoethyl, 2-piperidinoethyl, 2-pyrrolidinoethyl, N-methyl-N'-piperazinoethyl, 2-cyanoethyl, 2-hydroxyethyl, 2-methoxyethyl, 2-acetoxyethyl, 2-phenoxyacetoxyethyl, N-ethylcarbamoyloxyethyl, N-phenylcarbamoyloxyethyl, 2-phenoxyethyl, 3-methoxypropyl, 3-methylbenzyl, 2-methylphenyl, 4-methylphenyl, 2,4-dimethylphenyl, 2-chloro-4-methylphenyl, 2-chlorophenyl, 4-chlorophenyl, 2-methoxyphenyl, 4-methoxyphenyl, 2,5-dimethyl-4-chlorophenyl.

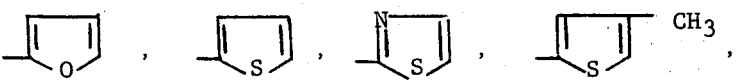

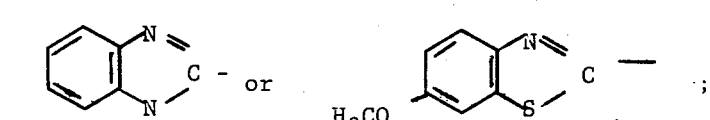

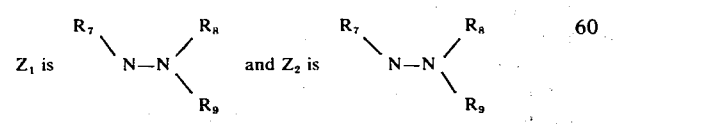

wherein $R_7$ is hydrogen, alkyl having 1 to 6 carbon atoms or phenyl and $R_8$ and $R_9$ taken separately are alkyl having 1 to 6 carbon atoms or phenyl and taken together with the nitrogen atom to which they are attached form a morpholino, pyrrolidino, piperidino or piperazino radical.

2. The compound of claim 1 wherein X is alkyl having 1 to 6 carbon atoms, alkenyl having 2 to 6 carbon atoms, cycloalkyl having 3 to 8 carbon atoms, phenyl, benzyl, phenethyl or hydrogen; $R_8$ and $R_9$ taken separately are alkyl having 1 to 6 carbon atoms or phenyl and taken together with the nitrogen atom to which they are attached form a morpholino radical.

3. The compound of claim 1 wherein $Z_1$ is the same as $Z_2$.

4. The compound of claim 1 wherein X is methyl.

5. The compound of claim 1 wherein X is methyl and $Z_1$ and $Z_2$ are

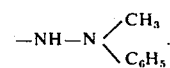

6. The compound of claim 1 wherein X is methyl and $Z_1$ and $Z_2$ are

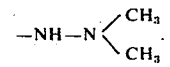

7. The compound of claim 1 wherein X is methyl and $Z_1$ and $Z_2$ are

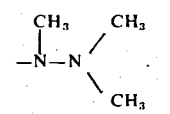

8. The compound of claim 1 wherein X is methyl and $Z_1$ and $Z_2$ are

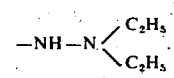

9. The compound of claim 1 wherein X is methyl and $Z_1$ and $Z_2$ are

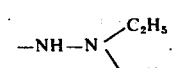

10. The compound of claim 1 wherein X is methyl and $Z_1$ and $Z_2$ are

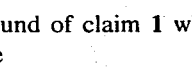

* * * * *